US011365177B2

(12) United States Patent
Spiegelman et al.

(10) Patent No.: US 11,365,177 B2
(45) Date of Patent: Jun. 21, 2022

(54) CHEMICAL UNCOUPLERS OF RESPIRATION AND METHODS OF USE THEREOF

(71) Applicants: Dana-Farber Cancer Institute, Inc., Boston, MA (US); The Scripps Research Institute, La Jolla, CA (US)

(72) Inventors: Bruce M. Spiegelman, Waban, MA (US); Jonathan Z. Long, Menlo Park, CA (US); Hua Lin, Jupiter, FL (US); Theodore Kamenecka, Palm Beach Gardens, FL (US); Patrick Griffin, Jupiter, FL (US)

(73) Assignees: Dana-Farber Cancer Institute, Inc., Boston, MA (US); University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/768,211

(22) PCT Filed: Nov. 29, 2018

(86) PCT No.: PCT/US2018/062974
§ 371 (c)(1),
(2) Date: May 29, 2020

(87) PCT Pub. No.: WO2019/108739
PCT Pub. Date: Jun. 6, 2019

(65) Prior Publication Data
US 2020/0317613 A1    Oct. 8, 2020

Related U.S. Application Data

(60) Provisional application No. 62/592,611, filed on Nov. 30, 2017.

(51) Int. Cl.
*C07D 211/60* (2006.01)
*A61P 29/02* (2006.01)
*C07D 209/42* (2006.01)
*C07D 215/48* (2006.01)
*C07D 217/22* (2006.01)

(52) U.S. Cl.
CPC ............ *C07D 211/60* (2013.01); *A61P 29/02* (2018.01); *C07D 209/42* (2013.01); *C07D 215/48* (2013.01); *C07D 217/22* (2013.01)

(58) Field of Classification Search
CPC .. C07D 211/60; C07D 209/42; C07D 215/48; C07D 217/22; A61P 29/02
See application file for complete search history.

(56) References Cited

U.S. PATENT DOCUMENTS

| 5,266,576 | A | 11/1993 | Vincent et al. | |
|---|---|---|---|---|
| 2007/0154439 | A1 | 7/2007 | Dorf | |
| 2010/0144827 | A1 | 6/2010 | Nassar et al. | |
| 2010/0260813 | A1* | 10/2010 | Schnabel | A01N 61/00 424/408 |
| 2013/0158070 | A1* | 6/2013 | Nassar | C07C 309/15 514/302 |
| 2014/0056953 | A1* | 2/2014 | Foeger | A61K 47/183 424/400 |
| 2015/0250882 | A1* | 9/2015 | Reslow | A61K 47/183 514/11.4 |
| 2016/0120995 | A1* | 5/2016 | Nassar | C07D 209/26 514/423 |

FOREIGN PATENT DOCUMENTS

WO    WO-2019/108739 A1    6/2019

OTHER PUBLICATIONS

Leishman, Biochimica et Biophysica Acta 1861, 491-500, 2016. (Year: 2016).*
Joslin Diabetes Center, Science Daily, Apr. 2021, pp. 1-3. (Year: 2021).*
Gregory, https://www.geneticgnews.com/wp content/uploads/2018/11/Nov27_2018_DavidGregoryDebbieMarshall_brwonFatCels-e1618433582905.jpg) (Year: 2018).*
Thoonen, Am J Physiol Heart Circ Physiol, vol. 310(11), H1592-H1605, 2016. (Year: 2016).*
Tortoriello, PLOS One, Jul. 2013, vol. 8 (7), e67865, pp. 1-10. (Year: 2013).*
Argiles, Int J Blochem & Cell Biology, vol. 35, 405-409, 2003. (Year: 2006).*
Bing, Brit J Cancer, vol. 86, 612-618, 2002. (Year: 2002).*
International Search Report and Written Opinion for International Application No. PCT/US2018/062974 dated Mar. 26, 2019.
Lin et al., "Discovery of hydrolysis-resistant isoindoline N-Acyl amino acid analogues that stimulate mitochondrial respiration," Journal of Medicinal Chemistry, 61:3224-3230 (2018).

* cited by examiner

*Primary Examiner* — D Margaret M Seaman
(74) *Attorney, Agent, or Firm* — Foley Hoag LLP

(57) ABSTRACT

Uncoupling of respiration is a well-recognized process that increases respiration and heat production in cells. Provided herein are chemical uncouplers of respiration that are compounds of Formula (I). Also provided are methods for preventing or treating metabolic disorders and modulating metabolic processes using compound of Formula (I).

19 Claims, 6 Drawing Sheets

CHEMICAL UNCOUPLERS OF RESPIRATION AND METHODS OF USE THEREOF

RELATED APPLICATIONS

This application is the U.S. national phase of International Patent Application No PCT/US2018/062974, filed on Nov. 29, 2018, which claims the benefit of priority to U.S. Provisional Patent Application Ser. No. 62/592,611, filed on Nov. 30, 2017. The entire contents of each of which are hereby incorporated by reference in their entirety.

GOVERNMENT SUPPORT

This invention was made with government support under Grant K99DK105203 awarded by the National Institutes of Health. The government has certain rights in the invention.

BACKGROUND

Metabolic disorders comprise a collection of health disorders or risks that increase the risk of morbidity and loss of qualify of life. For example, diabetes, obesity, including central obesity (disproportionate fat tissue in and around the abdomen), atherogenic dyslipidemia (including a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are all metabolic disorders collectively afflicting greater than 50 million people in the United States.

Brown fat has attracted significant interest as an antidiabetic (e.g., anti-type 2 diabetes) and anti-obesity tissue owing to its ability to dissipate energy as heat (Cannon and Nedergaard (2004) *Physiol. Rev.* 84:277-359; Harms and Seale (2013) *Nat. Med.* 19:1252-1263). Activation of brown fat thermogenesis involves the induction of a program of genes, including uncoupling protein 1 (UCP1), which uncouples respiration and increases heat production in fat cells (Kozak and Harper (2000) *Annu. Rev. Nutr.* 20:339-363). Either ablation of brown or beige cells (Cohen et al. (2014) *Cell* 156:304-316; Lowell et al. (1993) *Nature* 366:740-742) or knockout (KO) of the Ucp1 gene (Feldmann et al. (2009) *Cell Metab.* 9:203-209) predisposes mice to obesity and diabetes. Conversely, increasing the number or activity of brown and beige cells is protective against weight gain and metabolic disease (Seale et al. (2011) *J. Clin. Invest.* 121:96-105).

Most studies of adaptive thermogenesis and thermogenic fat have centered upon the expression and function of UCP1. This protein catalyzes a "proton leak" whereby protons that are pumped out of the mitochondrial matrix in the electron transport chain (ETC) are transported back across the inner mitochondrial membrane (Nicholls et al. (1978) *Experientia Suppl.* 32:89-93; Rousset et al. (2004) *Diabetes* 53:5130-S135). This results in oxidative metabolism with no production of ATP, a process referred to as uncoupled respiration. While UCP1 is a very important part of adaptive thermogenesis, in principle, any biochemical process that requires energy and is not linked to energy storage or work can function as a thermogenic event. Indeed, data have emerged indicating that UCP1 is not the only mediator of this process (Kazak et al. (2015) *Cell* 163:643-655; Ukropec et al. (2006) *J. Biol. Chem.* 281:31894-31908). Moreover, other carriers of the mitochondrial SLC25 family, of which UCP1 is only one member (SLC25A7), also have the ability catalyze a proton leak across the inner mitochondrial membrane (Brand et al. (2005) *Biochem. J.* 392:353-362).

Any treatment for obesity has to reduce energy intake, increase energy expenditure or combine both effects. Respiration uncoupling agents such as carbonyl cyanide p-trifluoro-methoxyphenylhydrazone ("FCCP") are well known in the art as having dramatic weight loss inducing effects. However, such agents are also associated with high mortality and serious side effects. The negative effects of such compounds are linked to the severe drop in ATP levels caused by excessively high doses of uncoupling agents.

Despite decades of scientific research, few effective therapies have emerged to treat metabolic disorders. Current therapies for obesity predominantly lead to decreased energy intake by acting at satiety centers in the brain or by reducing the efficiency of intestinal absorption. Given the severity and prevalence of obesity related disorders, there exists a great need for the identification of an anti-obesity therapeutic.

SUMMARY

Uncoupling of respiration is a well-recognized process that increases respiration and heat production in cells. Chemical uncouplers, including N-acyl amino acids, increase energy expenditure and weight loss. Provided herein are chemical uncouplers of respiration that are compounds of Formula (I). Also provided are methods for preventing or treating metabolic disorders and modulating metabolic processes using compound of Formula (I).

In one aspect of the disclosure, provided herein are compounds of Formula (Id), or a pharmaceutically acceptable salt thereof:

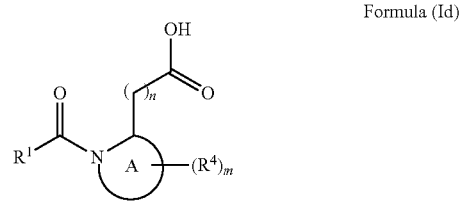

Formula (Id)

wherein ring A is a heterocycloalkyl or a heteroaryl;

$R^1$ is $(C_{10}-C_{30})$alkyl, $(C_{10}-C_{30})$alkene, or $(C_{10}-C_{30})$alkyne; $(C_{10}-C_{30})$alkyl, $(C_{10}-C_{30})$alkene, or $(C_{10}-C_{30})$alkyne is optionally substituted with one, two, three, or four substituents independently selected from the group consisting of $(C_1-C_6)$alkyl, $(C_1-C_6)$alkyloxy, cycloalkyl, and heterocycloalkyl;

$R^3$ is H or $(C_1-C_6)$alkyl;

$R^4$ is halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and N(R$^3$)—C(=NH)—N(R$^3$)$_2$;

m is an integer from 0-4; and n is an integer from 0-5.

In one aspect of the disclosure, provided herein is a method of preventing or treating a metabolic disorder in a subject comprising administering to the subject a therapeutically effective amount of compound represented by Formula (I), or a pharmaceutically acceptable salt thereof:

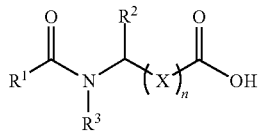

Formula (I)

wherein

X is —C($R^3$)$_2$—, —N($R^3$)—, —O—, —C(O)—, —C(O)O—, —OC(O)—, —C(O)N($R^3$)—, or —N($R^3$)C(O)—;

$R^1$ is ($C_{10}$-$C_{30}$)alkyl, ($C_{10}$-$C_{30}$)alkene, or ($C_{10}$-$C_{30}$)alkyne; wherein ($C_{10}$-$C_{30}$)alkyl, ($C_{10}$-$C_{30}$)alkene, or ($C_{10}$-$C_{30}$)alkyne is optionally substituted with one, two, three, or four substituents independently selected from the group consisting of ($C_1$-$C_6$)alkyl, ($C_1$-$C_6$)alkyloxy, cycloalkyl, and heterocycloalkyl;

$R^2$ is selected from the group consisting of H, ($C_1$-$C_6$)alkyl, ($C_1$-$C_6$)alkyloxy, cycloalkyl, heterocycloalkyl, aryl, heteroaryl, aralkyl, and heteroaralkyl, wherein ($C_1$-$C_6$)alkyl, ($C_1$-$C_6$)alkyloxy, cycloalkyl, heterocycloalkyl, aryl, heteroaryl, aralkyl, and heteroaralkyl is optionally substituted with one, two, three, or four substituents independently selected from the group consisting of halogen, —CN, —NO$_2$, —OR$^3$, —SR$^3$, —N($R^3$)$_2$, —($C_1$-$C_6$)alkyl, —C(O)OR$^3$, —C(O)N($R^3$)$_2$, —N($R^3$)C(O)R$^3$, —N($R^3$)C(O)OR$^3$, and N($R^3$)—C(=NH)—N($R^3$)$_2$;

or $R^2$ and —NR$^3$— taken together form a heterocycloalkyl or a heteroaryl, which is optionally substituted with one, two, three, or four substituents independently selected from the group consisting of halogen, —CN, —NO$_2$, —OR$^3$, —SR$^3$, —N($R^3$)$_2$, —($C_1$-$C_6$)alkyl, —C(O)OR$^3$, —C(O)N($R^3$)$_2$, —N($R^3$)C(O)R$^3$, —N($R^3$)C(O)OR$^3$, and N($R^3$)—C(=NH)—N($R^3$)$_2$;

$R^3$ is H or ($C_1$-$C_6$)alkyl; and n is an integer from 0-5, thereby preventing or treating the metabolic disorder in the subject.

In another aspect of the disclosure, provided herein is a method for modulating a metabolic response comprising contacting a cell with a compound represented by Formula (I), or a pharmaceutically acceptable salt thereof:

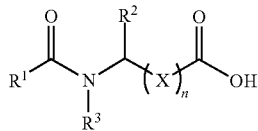

Formula (I)

wherein

X is —C($R^3$)$_2$—, —N($R^3$)—, —O—, —C(O)—, —C(O)O—, —OC(O)—, —C(O)N($R^3$)—, or —N($R^3$)C(O)—;

$R^1$ is ($C_{10}$-$C_{30}$)alkyl, ($C_{10}$-$C_{30}$)alkene, or ($C_{10}$-$C_{30}$)alkyne; wherein ($C_{10}$-$C_{30}$)alkyl, ($C_{10}$-$C_{30}$)alkene, or ($C_{10}$-$C_{30}$)alkyne is optionally substituted with one, two, three, or four substituents independently selected from the group consisting of ($C_1$-$C_6$)alkyl, ($C_1$-$C_6$)alkyloxy, cycloalkyl, and heterocycloalkyl;

$R^2$ is selected from the group consisting of H, ($C_1$-$C_6$)alkyl, ($C_1$-$C_6$)alkyloxy, cycloalkyl, heterocycloalkyl, aryl, heteroaryl, aralkyl, and heteroaralkyl, wherein ($C_1$-$C_6$)alkyl, ($C_1$-$C_6$)alkyloxy, cycloalkyl, heterocycloalkyl, aryl, heteroaryl, aralkyl, and heteroaralkyl is optionally substituted with one, two, three, or four substituents independently selected from the group consisting of halogen, —CN, —NO$_2$, —OR$^3$, —SR$^3$, —N($R^3$)$_2$, —($C_1$-$C_6$)alkyl, —C(O)OR$^3$, —C(O)N($R^3$)$_2$, —N($R^3$)C(O)R$^3$, —N($R^3$)C(O)OR$^3$, and N($R^3$)—C(=NH)—N($R^3$)$_2$;

or $R^2$ and —NR$^3$— taken together form a heterocycloalkyl or a heteroaryl, which is optionally substituted with one, two, three, or four substituents independently selected from the group consisting of halogen, —CN, —NO$_2$, —OR$^3$, —SR$^3$, —N($R^3$)$_2$, —($C_1$-$C_6$)alkyl, —C(O)OR$^3$, —C(O)N($R^3$)$_2$, —N($R^3$)C(O)R$^3$, —N($R^3$)C(O)OR$^3$, and N($R^3$)—C(=NH)—N($R^3$)$_2$;

$R^3$ is H or ($C_1$-$C_6$)alkyl; and n is an integer from 0-5, thereby modulating the metabolic response.

DETAILED DESCRIPTION

Figure 1:
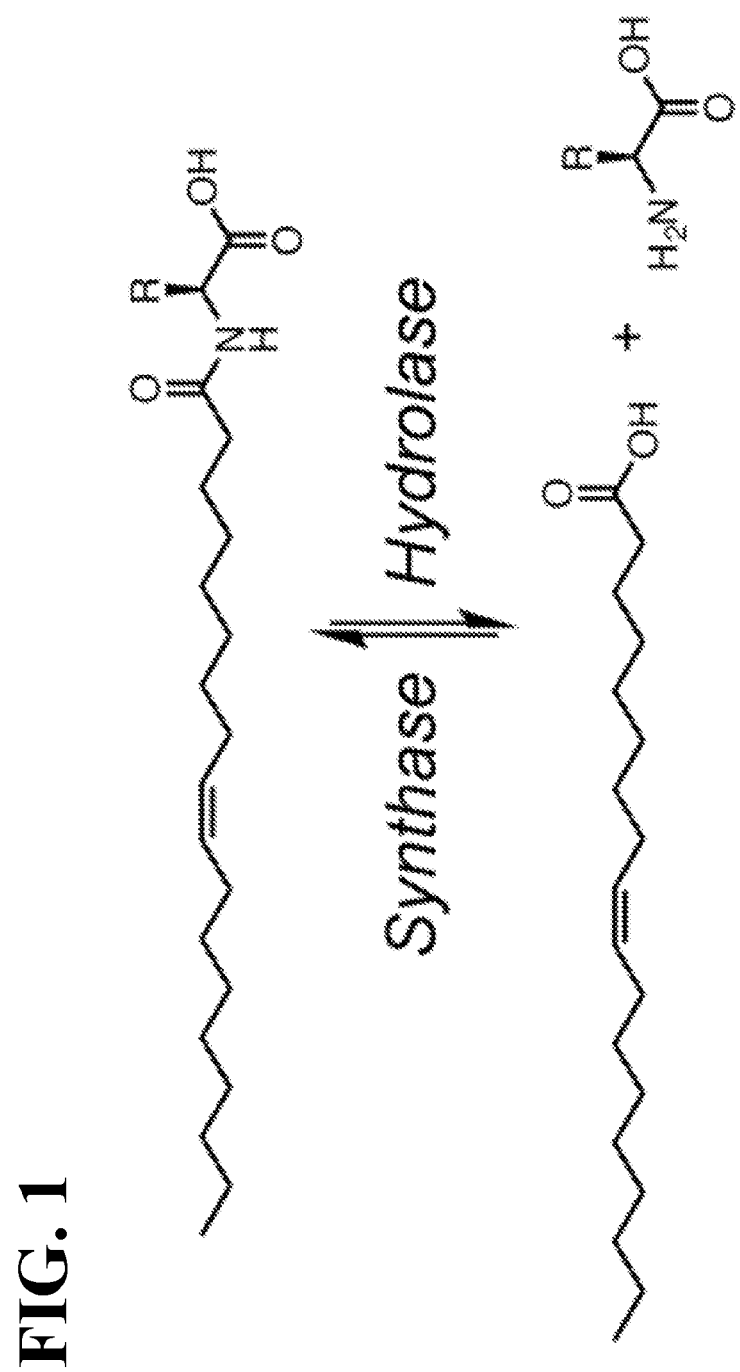
FIG. 1 shows a schematic of synthase and hydrolase reaction of free fatty acid and free amino acid to N-acyl amino acid by PM20D1.

Uncoupling of respiration is a well-recognized process that increases respiration and heat production in cells. This process can be stimulated by both proteins (e.g., UCP1) and small molecules (e.g., 2,4-dinitrophenol, "chemical uncouplers"). It is generally accepted that the increases in respiration are due to augmented proton flux through the inner mitochondrial membrane. Many studies since the 1920's have validated that chemical uncouplers can increase respiration in humans. In some embodiments, the chemical uncoupler belongs to a class of endogenous lipid metabolites, the N-acyl amino acids ("NAAs", e.g., N-arachidonoyl-glycine; N-oleoyl-leucine; N-oleoyl-phenylalanine, amongst others) (Long et al, Cell 2016). These lipid metabolites, when added to mitochondria, cells, or administered to mice, can increase oxygen consumption. In mice, administration of NAAs produced an increase in energy expenditure, profound weight loss, and improvement of glycemia. Furthermore, NAAs are enzymatically regulated by the circulating enzyme hormone peptidase M20 domain containing 1 (PM20D1). In some embodiments, the chemical uncoupler is an NAA analog or an NAA derivative. In some embodiments, the NAA analog or the NAA derivative is characterized by unnatural amino acid head groups. One representative member of these analogs is the compound 2-oleoylisoindoline-1-carboxylic acid.

In order that the present disclosure may be more readily understood, certain terms are first defined. Additional definitions are set forth throughout the detailed description.

The articles "a" and "an" are used herein to refer to one or to more than one (i.e. to at least one) of the grammatical object of the article. By way of example, "an element" means one element or more than one element.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 22 or fewer. For example, ($C_{10}$-$C_{22}$)alkyl. Likewise, preferred cycloalkyls have from 3-10 carbon atoms in their ring structure, and more preferably have 5, 6, or 7 carbons in the ring structure.

The term "alkene" refers to the radical of an unsaturated aliphatic group comprising at least one carbon-carbon double bond, including straight-chain alkene groups, branched-chain alkene groups, cycloalkene groups, alkene substituted cycloalkyl groups, and cycloalkyl substituted alkene groups.

The term "alkyne" refers to the radical of an unsaturated aliphatic group comprising at least one carbon-carbon triple bond, including straight-chain alkyne groups, branched-chain alkyne groups, cycloalkyne groups, alkyne substituted cycloalkyl groups, and cycloalkyl substituted alkyne groups.

The term "aralkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "carboxy" as used herein, means a —$CO_2H$ group.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio. The terms "arylthio," "alkenylthio" and "arylakylthio," for example, are likewise defined.

The term "amido" as used herein, means —NHC(=O)—, wherein the amido group is bound to the parent molecular moiety through the nitrogen. Examples of amido include alkylamido such as $CH_3C$(=O)N(H)— and $CH_3CH_2C$(=O)N(H)—.

The term "aryl" as used herein includes 5- to 14-membered aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryls" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl", "heterocycloalkyl", or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" or "halo" designates —F, —Cl, —Br or —I; the term "sulfhydryl" means —SH; the term "hydroxyl" means —OH; and the term "cyano" as used herein, means a —CN group.

The terms "amine" and "amino" are art recognized and refer to both unsubstituted and substituted amines, e.g., a moiety that can be represented by the general formula:

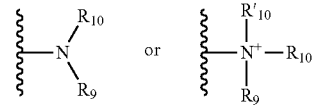

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this disclosure, the heteroatoms, such as nitrogen, may have hydrogen substituents and/or any permissible substituents of organic compounds described herein which satisfy the valencies of the heteroatoms.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

Naturally-occurring amino acids (L-form) are identified throughout the description and claims by the conventional three-letter abbreviations indicated in the below table.

TABLE 1

(Amino acid codes)

| Name | 3-letter code |
|---|---|
| Alanine | Ala |
| Arginine | Arg |
| Asparagine | Asn |
| Aspartic acid | Asp |
| Cysteine | Cys |
| Glutamic acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "administering" is intended to include routes of administration which allow the compound to perform its intended function of modulating (e.g., increasing or decreasing) expression and/or activity of PM20D1. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term "effective amount" of a compound that induces expression and/or activity of PM20D1 is that amount necessary or sufficient to modulate (e.g., increase or decrease) expression and/or activity of PM20D1 in the subject or population of subjects. The effective amount can vary depending on such factors as the type of compound(s) employed, the size of the subject, or the severity of the disorder.

The terms "beige fat" or "brite (brown in white) fat" or "iBAT (induced brown adipose tissue)" or "recruitable BAT (brown adipose tissue)" or "wBAT (white adipose BAT)" refer to clusters of UCP1-expressing adipocytes having thermogenic capacity that develop in white adipose tissue (WAT). Beige fat can develop in subcutaneous WAT, such as in inguinal WAT, or in intra-abdominal WAT such as in epididymal WAT. Similar to adipocytes in brown adipose tissue (BAT), beige cells are characterized by a) multilocular lipid droplet morphology, b), high mitochondrial content, and/or c) expression of a core set of brown fat-specific genes, such as Ucp1, Cidea, Pgc1a, and other listed in Table 2. BAT and beige fat both are able to undergo thermogenesis, but these are distinct cell types since beige cells do not derive from Myf5 precursor cells like BAT cells, beige fat express thermogenic genes only in response to activators like beta-adrenergic receptor or PPARgamma agonists unlike constitutive expression in BAT cells (Harms and Seale (2013) Nat. Med. 19:1252-1263).

The term "binding" or "interacting" refers to an association, which may be a stable association, between two molecules, e.g., between a compound of the disclosure and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intracellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

In some embodiments, "pain" is included within the term "metabolic disorder." Pain is a sensation and a perception that is comprised of a complex series of mechanisms. Pain can be experienced both acutely and chronically. Acute pain is the instantaneous onset of a painful sensation in response to a noxious stimulus. It is considered to be adaptive because it can prevent an organism from damaging itself in some instances. Unlike acute pain (e.g., the transient protective physiology pain), persistent pain (also called chronic pain) usually has a delayed onset but can last for hours to days, or even months or years. Persistent pain may involve an amalgamation of physical, social, and psychologic factors. Persistent pain occurs in a variety of forms including, but not limited to, spontaneous pain (painful sensation without an external stimulus), allodynia (painful sensation in response to a normally innocuous stimulus) and hyperalgesia (strong painful sensation to a mildly painful stimulus). Persistent pain can be caused by many different factors. For example, persistent pain can be caused by conditions that accompany the aging process (e.g., conditions that may affect bones and joints in ways that cause persistent pain). In some embodiments, persistent pain can be caused by inflammation or nerve injury (for example, damage to or malfunction of the nervous system). In some embodiments, persistent pain can be inflammatory pain or neuropathic pain (for example, peripheral neuropathic pain and central neuropathic pain). In some embodiments, persistent pain is mediated by hyperexcitable pain-processing neurons in peripheral and central nervous system (e.g., peripheral sensitization or central sensitization). Surrogate indicators of pain are well-known in the art and can be assayed using routine methods, such as hot plate or tail immersion assays to determine thermally-induced pain, electronic von Frey apparatus assays to determine mechanically-induced pain, acetic acid assays to determine chemically-induced pain, adjuvant injection assays to determine inflammatory pain, and the like.

The term "N-lipidated amino acid" includes natural and synthetic amino acids having a hydrophobic or amphiphilic group derivatized to an amine functional group. Natural amino acids comprise an amine ($NH_2$), a carboxylic acid (COOH), and a side chain (R). They are commonly classified according to the location of these core structural groups to core carbon atoms (e.g., alpha, beta, gamma, and delta amino acids). For example, amino acids having both an amine and carboxylic acid groups attached to the first carbon (i.e., alpha carbon) are known as alpha amino acids. The 22 natural proteinogenic amino acids are alpha amino acids (including the 20 natural proteinogenic amino acids encoded directly by triplet codons) and most are present in nature as the L-stereoisomer. By contrast, gamma-amino-butyric acid (GABA) is a gamma amino acid. In some embodiments, the hydrophobic or amphiphilic group is derivatized to the amine functional group of the main chain (i.e., backbone) alpha, beta, gamma, or delta carbon. In organic chemistry, the alpha carbon refers to the first carbon atom that attaches to a function group, whereas the second carbon atom is called the beta carbon, and so forth. For amino acids, the alpha carbon is the backbone carbon before the carbonyl carbon and is the stereo center for every amino acid except glycine. Moreover, L-stereoisomers, D-stereoisomers, and racemic mixtures are also contemplated. The hydrophobic or amphiphilic group can be a fatty acid, a fatty alcohol, a sterol such as cholesterol, and the like. The hydrophobic or amphiphilic group can be saturated, unsaturated, cis, trans, branched, linear, salt form, or any combination thereof, such as a linear fatty acid with 1, 2, 4, or 6 cis or trans carbon-carbon double bonds. The hydrophobic or amphiphilic group can have an even or uneven-number of double bonds, triple bonds, or carbon chains. In some embodiments, the hydrophobic or amphiphilic group can have a carbon chain length of $C_1$-$C_{30}$, such as $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, or longer, or any range in between inclusive, such as $C_{10}$-$C_{30}$, $C_{12}$-$C_{30}$, $C_{12}$-$C_{22}$, and the like. The hydrophobic or amphiphilic group can be derivatized as an acyl group such that the N-lipidated amino acid is an N-acyl amino acid. As described above, the acyl chain can be $C_{10}$-$C_{22}$ or any range in between inclusive, such as $C_{14}$, $C_{16}$, C16:1, $C_{18}$, C18:1, C18:2, C20:4, C22:6, and the like (such as N-arachidonoyl glycine, N-arachidonoyl phenylalanine, N-arachidonoyl serine, N-arachidonoyl gamma amino butyric acid, N-oleoyl phenylalanine, N-linoleoyl phenylalanine, N-stearoyl phenylalanine, and N-palmitoyl phenylalanine). Moreover, highly polyunsaturated or completely unsaturated or oxidatively-modified long chain acyl chains (e.g., $C_{24}$) are contemplated. The carboxylic acid group of the main chain carbon can be a carboxylic group in some embodiments. In other embodiments, the carboxylic acid group of the main chain carbon can be replaced with a terminal functional group having a pKa of approximately 4-5 including, without limitation, a carboxylate group, activated phenol group, phenoylhydrazone group, and the like. Without being bound by theory, it is believed that the terminal functional group having a pKa of approximately 4-5 or carboxylic group acts as a protein carrier in order to generate the UCP1-independent uncoupling effect. Any parameter or combination of parameters described above can be applied to an N-lipidated amino acid of the present disclosure.

As used herein, "obesity" refers to a body mass index (BMI) of 30 kg/m² or more (National Institute of Health, Clinical Guidelines on the Identification, Evaluation, and Treatment of Overweight and Obesity in Adults (1998)). However, the present disclosure is also intended to include a disease, disorder, or condition that is characterized by a body mass index (BMI) of 25 kg/m² or more, 26 kg/m² or more, 27 kg/m² or more, 28 kg/m² or more, 29 kg/m² or more, 29.5 kg/m² or more, or 29.9 kg/m² or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

As used herein, the term "PM20D1" or "Peptidase M20 Domain-Containing Protein 1" refers to the D1 family member of the M20A family of secreted peptidases and is intended to include fragments, variants (e.g., allelic variants) and derivatives thereof unless otherwise specified. PM20D1 proteins generally contain a metal ion coordination site and a peptidase domain (Brass et al. (2008) *Science* 319:921-926; Gonzales et al. (2009) *J. Am. Soc. Nephrol.* 20:363-379; Satake et al. (2009) *Nat. Genet.* 41:1303-1307; and Sung et al. (2013) *Hum. Genet.* 132:423-429). PM20D1 has not heretofore been implicated in the regulation of cellular metabolism. Mature PM20D1 proteins lack a signal sequence and PM20D1 sequences of the present disclosure can comprise a signal sequence, as well as lack a signal sequence. The PM20D1 signal sequence is generally the most N-terminal 20, 21, 22, 23, 24, 25, 26, 27, 28, 29, or 30 amino acids.

Representative PM20D1 nucleic acid and protein sequences are well-known in the art. For example, representative human PM20D1 cDNA and amino acid sequences can be obtained from the National Center for Biotechnology Information (NCBI) under accession numbers NM_152491.4 and NP_689704.4, respectively.

In some embodiments, fragments of PM20D1 having one or more biological activities of the full-length PM20D1 protein are described and employed. Such fragments can comprise or consist of at least one domain of a PM20D1 protein without containing the full-length PM20D1 protein sequence. In some embodiments, PM20D1 fragments can comprise, or consist of, an M20 peptidase domain (e.g., residues 53-487 of human PM20D1), a metal ion binding site (e.g., residues 125, 157, 191, 192, 217, and 464 of human PM20D1) and the like, without containing the full-length PM20D1 protein sequence.

Compounds

In some embodiments, the chemical uncoupler is a compound having the structural formula of Formula (I), or a pharmaceutically acceptable salt thereof. In some embodiments, the compound is represented by Formula (I), or a pharmaceutically acceptable salt thereof:

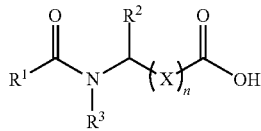

Formula (I)

wherein

X is $-C(R^3)_2-$, $-N(R^3)-$, $-O-$, $-C(O)-$, $-C(O)O-$, $-OC(O)-$, $-C(O)N(R^3)-$, or $-N(R^3)C(O)-$;

$R^1$ is $(C_{10}-C_{30})$alkyl, $(C_{10}-C_{30})$alkene, or $(C_{10}-C_{30})$alkyne; wherein $(C_{10}-C_{30})$alkyl, $(C_{10}-C_{30})$alkene, or $(C_{10}-C_{30})$alkyne is optionally substituted with one, two, three, or four substituents independently selected from the group consisting of $(C_1-C_6)$alkyl, $(C_1-C_6)$alkyloxy, cycloalkyl, and heterocycloalkyl;

$R^2$ is selected from the group consisting of H, $(C_1-C_6)$alkyl, $(C_1-C_6)$alkyloxy, cycloalkyl, heterocycloalkyl, aryl, heteroaryl, aralkyl, and heteroaralkyl, wherein $(C_1-C_6)$alkyl, $(C_1-C_6)$alkyloxy, cycloalkyl, heterocycloalkyl, aryl, heteroaryl, aralkyl, and heteroaralkyl is optionally substituted with one, two, three, or four substituents independently selected from the group consisting of halogen, $-CN$, $-NO_2$, $-OR^3$, $-SR^3$, $-N(R^3)_2$, $-(C_1-C_6)$alkyl, $-C(O)OR^3$, $-C(O)N(R^3)_2$, $-N(R^3)C(O)R^3$, $-N(R^3)C(O)OR^3$, and $N(R^3)-C(=NH)-N(R^3)_2$;

or $R^2$ and $-NR^3-$ taken together form a heterocycloalkyl or a heteroaryl, which is optionally substituted with one, two, three, or four substituents independently selected from the group consisting of halogen, $-CN$, $-NO_2$, $-OR^3$, $-SR^3$, $-N(R^3)_2$, $-(C_1-C_6)$alkyl, $-C(O)OR^3$, $-C(O)N(R^3)_2$, $-N(R^3)C(O)R^3$, $-N(R^3)C(O)OR^3$, and $N(R^3)-C(=NH)-N(R^3)_2$;

$R^3$ is H or $(C_1-C_6)$alkyl; and n is an integer from 0-5.

In some embodiments of the compound of Formula (I), $R^1$ is $(C_{10}-C_{22})$alkyl or $(C_{10}-C_{22})$alkene; wherein $(C_{10}-C_{22})$alkyl or $(C_{10}-C_{22})$alkene is optionally substituted with one, two, three, or four substituents independently selected from the group consisting of $(C_1-C_6)$alkyl and cycloalkyl;

$R^2$ is selected from the group consisting of H, $(C_1-C_6)$alkyl, $(C_1-C_6)$alkyloxy, cycloalkyl, heterocycloalkyl, aryl, heteroaryl, aralkyl, and heteroaralkyl, wherein $(C_1-C_6)$alkyl, $(C_1-C_6)$alkyloxy, cycloalkyl, heterocycloalkyl, aryl, heteroaryl, aralkyl, and heteroaralkyl is optionally substituted with one or two substituents independently selected from the group consisting of $-OR^3$, $-SR^3$, $-N(R^3)_2$, $-(C_1-C_6)$alkyl, $-C(O)N(R^3)_2$, and $-N(R^3)C(O)R^3$;

or $R^2$ and $-NR^3-$ taken together form a heterocycloalkyl or a heteroaryl, which is optionally substituted with one or two substituents independently selected from the group consisting of $-OR^3$, $-SR^3$, $-N(R^3)_2$, $-(C_1-C_6)$alkyl, $-C(O)N(R^3)_2$, and $-N(R^3)C(O)R^3$;

$R^3$ is H or $(C_1-C_6)$alkyl; and n is an integer from 0-3.

In some embodiments of the compound of Formula (I), $R^1$ is $(C_{12}-C_{22})$alkyl or $(C_{12}-C_{22})$alkene;

$R^2$ is selected from the group consisting of H, $(C_1-C_6)$alkyl, cycloalkyl, heterocycloalkyl, aryl, heteroaryl, aralkyl, and heteroaralkyl, wherein $(C_1-C_6)$alkyl, cycloalkyl, heterocycloalkyl, aryl, heteroaryl, aralkyl, and heteroaralkyl is optionally substituted with one or two substituents independently selected from the group consisting of $-(C_1-C_6)$alkyl, $-C(O)N(R^3)_2$, and $-N(R^3)C(O)R^3$;

or $R^2$ and $-NR^3-$ taken together form a heterocycloalkyl or a heteroaryl, which is optionally substituted with one or two substituents independently selected from the group consisting of $-(C_1-C_6)$alkyl, $-C(O)N(R^3)_2$, and $-N(R^3)C(O)R^3$;

$R^3$ is H or $(C_1-C_6)$alkyl; and n is an integer from 0-3.

In some embodiments of the compounds disclosed herein, X is $-C(R^3)_2-$, $-N(R^3)-$, $-O-$, $-C(O)N(R^3)-$, or $-N(R^3)C(O)-$. In some embodiments, X is $-C(R^3)_2-$ or $-C(O)N(R^3)-$. In some embodiments, X is $-C(O)N(R^3)-$. In some embodiments, X is $-C(R^3)_2-$.

In some embodiments, the compound of Formula (I) is represented by Formula (Ia) or a pharmaceutically acceptable salt thereof:

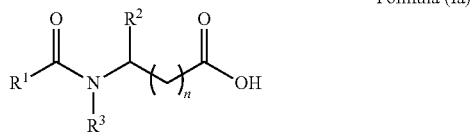

Formula (Ia)

wherein the variables are defined as described above and below.

In some embodiments of the compound of Formula (Ia), $R^1$ is $(C_{10}-C_{22})$alkyl or $(C_{10}-C_{22})$alkene; wherein $(C_{10}-C_{22})$alkyl or $(C_{10}-C_{22})$alkene is optionally substituted with one or two substituents independently selected from the group consisting of $(C_1-C_6)$alkyl and cycloalkyl;

$R^2$ is selected from the group consisting of H, $(C_1-C_6)$alkyl, $(C_1-C_6)$alkyloxy, cycloalkyl, heterocycloalkyl, aryl, heteroaryl, aralkyl, and heteroaralkyl, wherein $(C_1-C_6)$alkyl, $(C_1-C_6)$alkyloxy, cycloalkyl, heterocycloalkyl, aryl, heteroaryl, aralkyl, and heteroaralkyl is optionally substituted with one or two substituents independently selected from the group consisting of —$OR^3$, —$SR^3$, —$N(R^3)_2$, —$(C_1-C_6)$alkyl, —$C(O)N(R^3)_2$, and —$N(R^3)C(O)R^3$; or $R^2$ and —$NR^3$— taken together form a heterocycloalkyl or a heteroaryl, which is optionally substituted with one or two substituents independently selected from the group consisting of —$OR^3$, —$SR^3$, —$N(R^3)_2$, —$(C_1-C_6)$alkyl, —$C(O)N(R^3)_2$, and —$N(R^3)C(O)R^3$;

$R^3$ is H or $(C_1-C_6)$alkyl; and n is an integer from 0-3.

In some embodiments of the compound of Formula (Ia), $R^1$ is $(C_{14}-C_{22})$alkyl or $(C_{14}-C_{22})$alkene;

$R^2$ is selected from the group consisting of H, $(C_1-C_6)$alkyl, cycloalkyl, heterocycloalkyl, aryl, heteroaryl, aralkyl, and heteroaralkyl, wherein $(C_1-C_6)$alkyl, cycloalkyl, heterocycloalkyl, aryl, heteroaryl, aralkyl, and heteroaralkyl is optionally substituted with one or two substituents independently selected from the group consisting of —$(C_1-C_6)$alkyl, —$C(O)N(R^3)_2$, and —$N(R^3)C(O)R^3$; or $R^2$ and —$NR^3$— taken together form a heterocycloalkyl or a heteroaryl, which is optionally substituted with one or two substituents independently selected from the group consisting of —$(C_1-C_6)$alkyl, —$C(O)N(R^3)_2$, and —$N(R^3)C(O)R^3$;

$R^3$ is H or $(C_1-C_6)$alkyl; and n is an integer from 0-3.

In some embodiments of the compounds disclosed herein, $R^1$ is $(C_{10}-C_{22})$alkyl or $(C_{10}-C_{22})$alkene. In some embodiments, $R^1$ is $(C_{12}-C_{22})$alkyl or $(C_{12}-C_{22})$alkene. In some embodiments, $R^1$ is $(C_{16}-C_{20})$alkyl or $(C_1-C_2)$alkene. In some embodiments, $R^1$ is selected from the group consisting of $C_{12}$, $C_{14}$, $C_{16}$, C16:1, $C_{18}$, C18:1, C18:2, C18:3, $C_{20}$, C20:1, C20:4, C20:5, $C_{22}$, C22:1, and C22:6.

In some embodiments of the compounds disclosed herein, $(C_{10}-C_{22})$alkyl, $(C_{10}-C_{22})$alkene, or $(C_{10}-C_{22})$alkyne is substituted with one or two substituents independently selected from the group consisting of $(C_1-C_6)$alkyl, $(C_1-C_6)$alkyloxy, cycloalkyl, and heterocycloalkyl. In some embodiments, the one or two substituents are independently selected from $(C_1-C_6)$alkyl or cycloalkyl. In some embodiments, the one or two substituents are $(C_1-C_6)$alkyl.

In some embodiments of the compounds disclosed herein, $R^2$ is selected from the group consisting of H, $(C_1-C_6)$alkyl, heterocycloalkyl, aryl, heteroaryl, aralkyl, and heteroaralkyl. In some embodiments, $R^2$ is selected from the group consisting of H, $(C_1-C_6)$alkyl, aralkyl, and heteroaralkyl.

In some embodiments of the compounds disclosed herein, $(C_1-C_6)$alkyl, $(C_1-C_6)$alkyloxy, cycloalkyl, heterocycloalkyl, aryl, heteroaryl, aralkyl, and heteroaralkyl is substituted with one or two substituents independently selected from the group consisting of halogen, —CN, —$NO_2$, —$OR^3$, —$SR^3$, —$N(R^3)_2$, —$(C_1-C_6)$alkyl, —$C(O)OR^3$, —$C(O)N(R^3)_2$, —$N(R^3)C(O)R^3$, and —$N(R^3)C(O)OR^3$. In some embodiments, the one or two substituents are independently selected from the group consisting of halogen, CN, —$NO_2$, —$OR^3$, —$SR^3$, and $(C_1-C_6)$alkyl. In some embodiments, the one or two substituents are independently selected from the group consisting of —$OR^3$, —$SR^3$, and $(C_1-C_6)$alkyl. In some embodiments, the one or two substituents are independently selected from the group consisting of —OH, —SH, and $(C_1-C_6)$alkyl.

In some embodiments, $R^2$ represents a side chain of a natural or an unnatural amino acid. In some embodiments, $R^2$ represents a neutral side chain of a natural or an unnatural amino acid.

In some embodiments of the compounds disclosed herein, n is 0, 1, 2, or 3. In some embodiments, n is 0.

In some embodiments, the compound of Formula (I) is represented by Formula (Ib) or a pharmaceutically acceptable salt thereof:

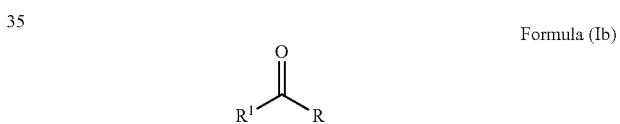

Formula (Ib)

wherein $R^1$ is $(C_{10}-C_{22})$alkyl, $(C_{10}-C_{22})$alkene, or $(C_{10}-C_{22})$alkyne; wherein $(C_{10}-C_{22})$alkyl, $(C_{10}-C_{22})$alkene, or $(C_{10}-C_{22})$alkyne is optionally substituted with one, two, three, or four substituents independently selected from the group consisting of $(C_1-C_6)$alkyl, $(C_1-C_6)$alkyloxy, cycloalkyl, and heterocycloalkyl; and R represents a natural or an unnatural amino acid.

In some embodiments, the compound of Formula (Ib) is a compound of Formula (Ic), wherein $R^1$ is $(C_{10}-C_{22})$alkyl or $(C_{10}-C_{22})$alkene; wherein $(C_{10}-C_{22})$alkyl or $(C_{10}-C_{22})$alkene is optionally substituted with one, two, three, or four substituents independently selected from the group consisting of $(C_1-C_6)$alkyl, $(C_1-C_6)$alkyloxy, cycloalkyl, and heterocycloalkyl; and R is selected from the group consisting of Ala, Asn, Cys, Gln, Gly, His, Ile, Leu, Met, Phe, Pro, Ser, Thr, Trp, Tyr, Val, Gly-Gly, and homoglycine.

The amino acids can be L-stereoisomers, D-stereoisomers, or racemic mixtures.

In some embodiments, the chemical uncoupler belongs to a class of endogenous lipid metabolites, the N-acyl amino acids ("NAAs", e.g., N-arachidonoyl-glycine; N-oleoyl-leucine; N-oleoyl-phenylalanine, amongst others) (Long et al, Cell 2016). In some embodiments, the chemical uncoupler is N-arachidonoyl-glycine; N-oleoyl-leucine; or N-oleoyl-phenylalanine.

In some embodiments, R represents a natural amino acid. In some embodiments, R is selected from the group consisting of Ala, Asn, Cys, Gln, Gly, His, Ile, Leu, Met, Phe, Pro, Ser, Thr, Trp, Tyr, and Val. In some embodiments, R is selected from the group consisting of Ala, Asn, Gln, Gly, His, Ile, Leu, Phe, Pro, Ser, Thr, Trp, Tyr, and Val. In some embodiments, R is selected from the group consisting of Asn, Gln, Gly, Ile, Leu, Phe, Pro, Trp, and Val. In some embodiments, R is selected from the group consisting of Gly, Leu, and Pro.

In some embodiments, the chemical uncoupler is an NAA analog or an NAA derivative. In some embodiments, the NAA analog or the NAA derivative is characterized by unnatural amino acid head groups. One representative member of these analogs is the compound 2-oleoylisoindoline-1-carboxylic acid. In some embodiments, R represents D-Phe, Gly-Gly, or homoglycine. In some embodiments, R represents Gly-Gly or homoglycine.

In some embodiments, the chemical uncoupler is an isoindoline NAA analog. In some embodiments, the chemical uncoupler is a proline-derived or homoproline-derived NAA analog.

In some embodiments, $R^2$ and $-NR^3-$ taken together form a heterocycloalkyl or a heteroaryl, which is optionally substituted with one, two, three, or four substituents independently selected from the group consisting of halogen, $-CN$, $-NO_2$, $-OR^3$, $-SR^3$, $-N(R^3)_2$, $-(C_1-C_6)$alkyl, $-C(O)OR^3$, $-C(O)N(R^3)_2$, $-N(R^3)C(O)R^3$, $-N(R^3)C(O)OR^3$, and $N(R^3)-C(=NH)-N(R^3)_2$. In some embodiments, the compound of Formula (I) is represented by Formula (Id) or a pharmaceutically acceptable salt thereof:

Formula (Id)

wherein
ring A is a heterocycloalkyl or a heteroaryl;
$R^1$ is $(C_{10}-C_{30})$alkyl, $(C_{10}-C_{30})$alkene, or $(C_{10}-C_{30})$alkyne; $(C_{10}-C_{30})$alkyl, $(C_{10}-C_{30})$alkene, or $(C_{10}-C_{30})$alkyne is optionally substituted with one, two, three, or four substituents independently selected from the group consisting of $(C_1-C_6)$alkyl, $(C_1-C_6)$alkyloxy, cycloalkyl, and heterocycloalkyl;
$R^3$ is H or $(C_1-C_6)$alkyl;
$R^4$ is halogen, $-CN$, $-NO_2$, $-OR^3$, $-SR^3$, $-N(R^3)_2$, $-(C_1-C_6)$alkyl, $-C(O)OR^3$, $-C(O)N(R^3)_2$, $-N(R^3)C(O)R^3$, $-N(R^3)C(O)OR^3$, and $N(R^3)-C(=NH)-N(R^3)_2$;
m is an integer from 0-4; and
n is an integer from 0-5.

In some embodiments of the compound of Formula (Id), $R^1$ is $(C_{12}-C_{22})$alkyl or $(C_{12}-C_{22})$alkene; wherein $(C_{12}-C_{22})$alkyl or $(C_{12}-C_{22})$alkene is optionally substituted with one or two substituents independently selected from the group consisting of $(C_1-C_6)$alkyl and cycloalkyl;
$R^3$ is H or $(C_1-C_6)$alkyl;
$R^4$ is halogen, $-CN$, $-NO_2$, $-OR^3$, $-SR^3$, $-N(R^3)_2$, $-(C_1-C_6)$alkyl, $-C(O)OR^3$, $-C(O)N(R^3)_2$, $-N(R^3)C(O)R^3$, $-N(R^3)C(O)OR^3$, and $N(R^3)-C(=NH)-N(R^3)_2$; and
m is an integer from 0-2; and
n is an integer from 0-3.

In some embodiments of the compound of Formula (Id), $R^1$ is $(C_{12}-C_{22})$alkyl or $(C_{12}-C_{22})$alkene;
$R^3$ is H or $(C_1-C_6)$alkyl;
$R^4$ is halogen, $-CN$, $-NO_2$, $-OR^3$, $-SR^3$, $-N(R^3)_2$, $-(C_1-C_6)$alkyl, $-C(O)OR^3$, $-C(O)N(R^3)_2$, $-N(R^3)C(O)R^3$, $-N(R^3)C(O)OR^3$, and $N(R^3)-C(=NH)-N(R^3)_2$;
m is an integer from 0-4; and
n is an integer from 0-3.

In some embodiments, each $R^4$ is independently selected from the group consisting of halogen, CN, $-NO_2$, $-OR^3$, $-SR^3$, and $(C_1-C_6)$alkyl. In some embodiments, each $R^4$ is independently selected from the group consisting of $-OR^3$, $-SR^3$, and $(C_1-C_6)$alkyl. In some embodiments, each $R^4$ is independently selected from the group consisting of $-OH$, $-SH$, and $(C_1-C_6)$alkyl.

In some embodiments, ring A is unsubstituted. In some embodiments, m is 0. In some embodiments, n is 0. In some embodiments of the compound of Formula (Id),
$R^1$ is $(C_{10}-C_{22})$alkyl or $(C_{10}-C_{22})$alkene;
m is 0; and
n is 0.

In some embodiments, ring A is selected from the group consisting of

In some embodiments, the compound of Formula (Id) is selected from the group consisting of
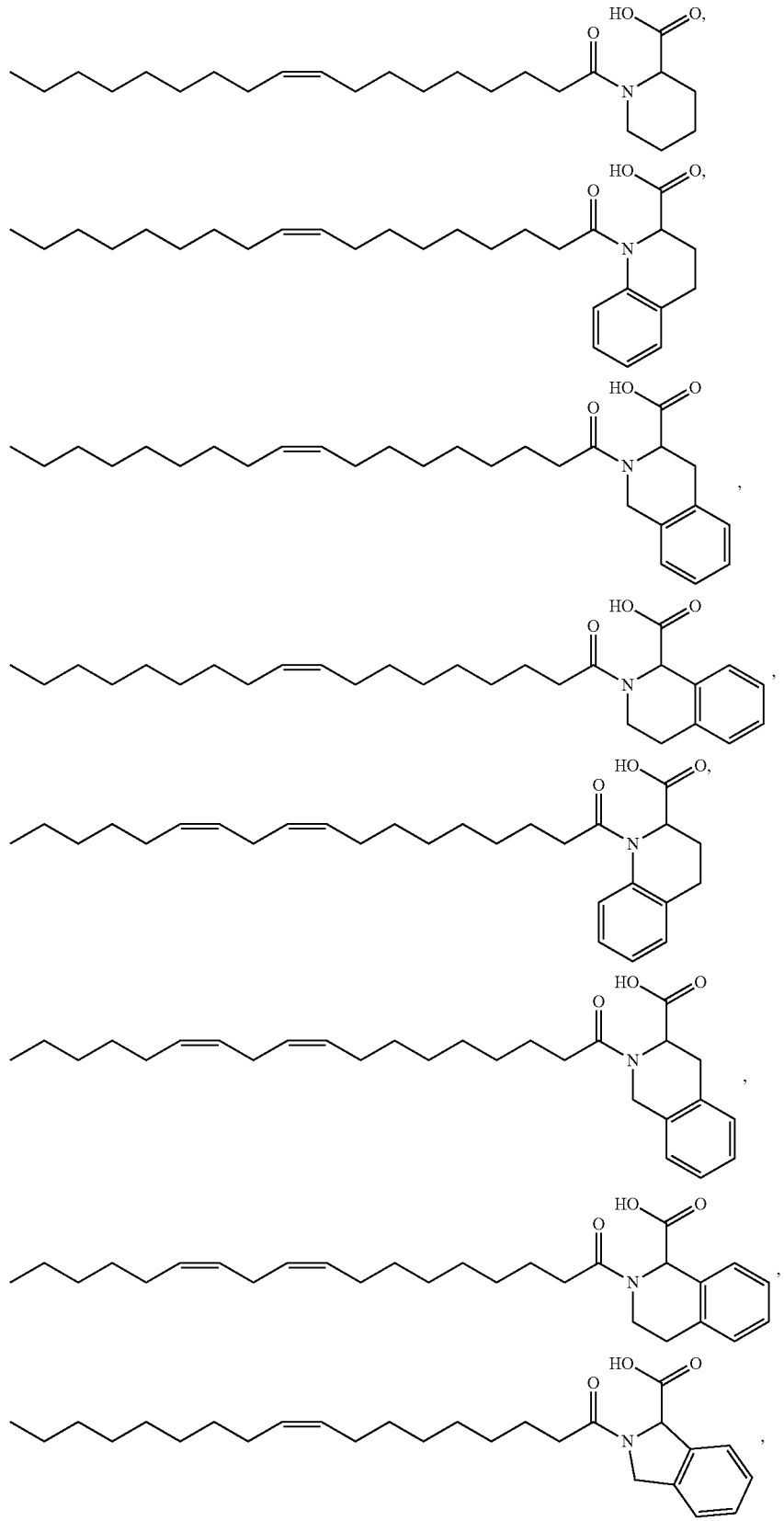

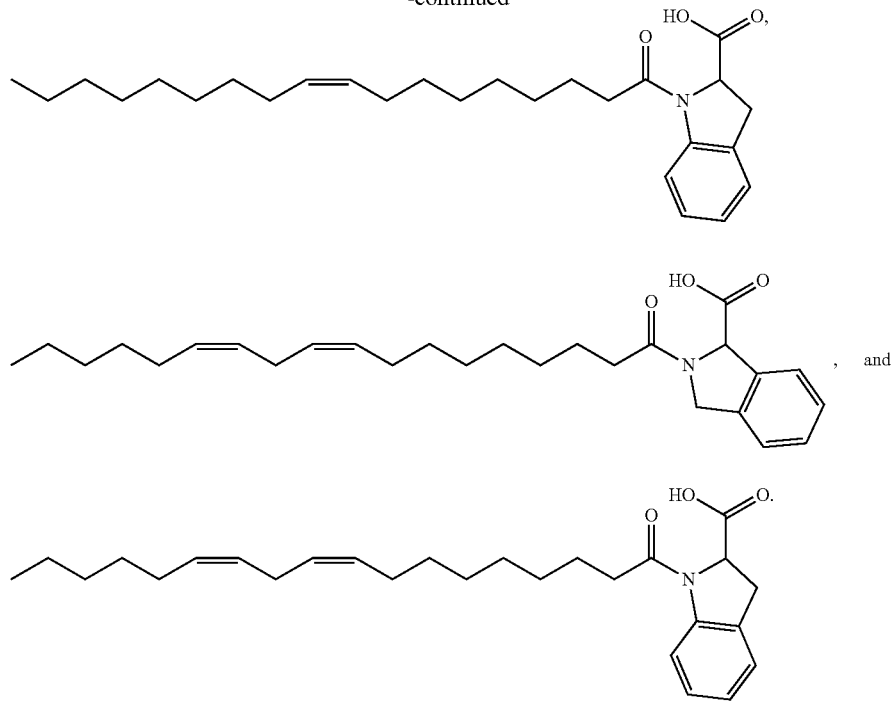
In some embodiments, the compound of Formula (Id) is selected from the group consisting of
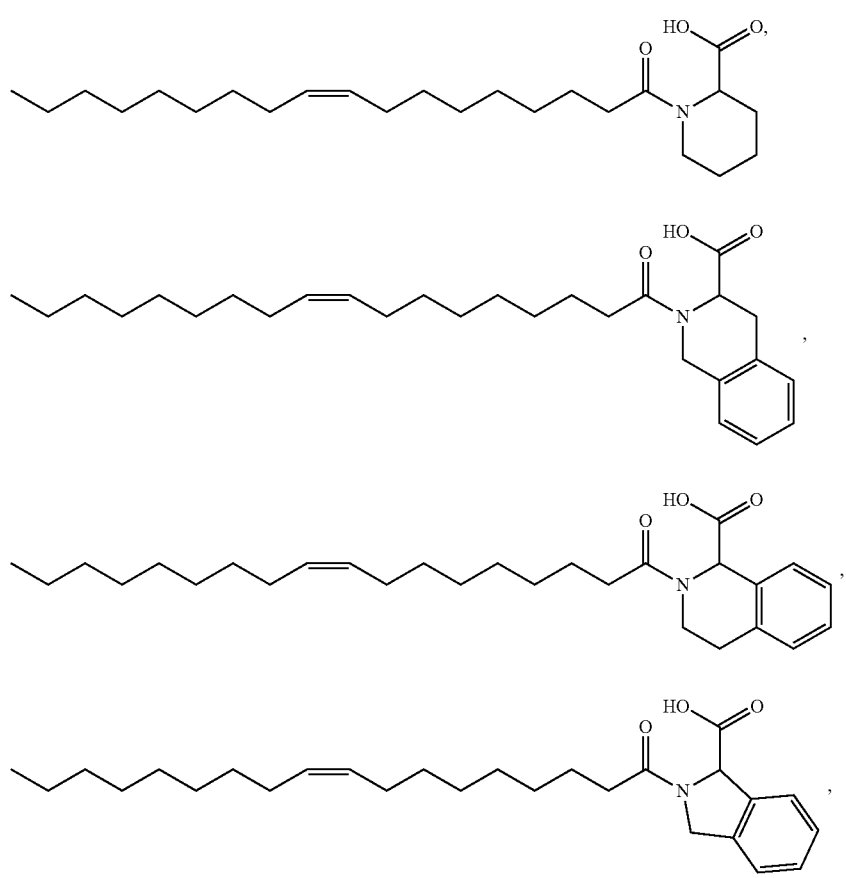

-continued

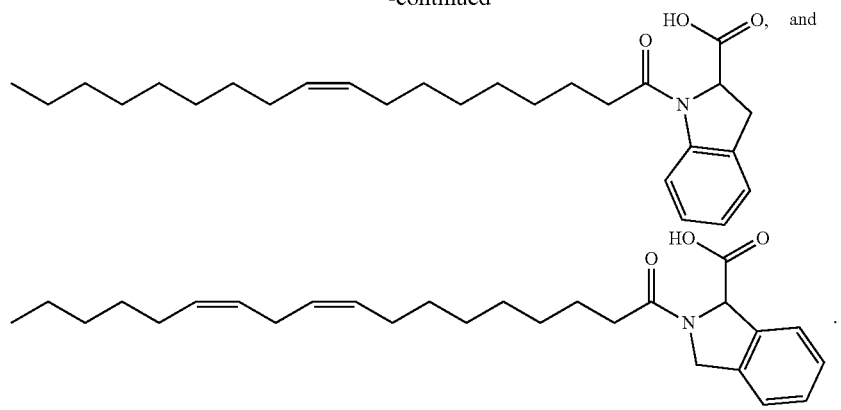

In some embodiments, the compound of Formula (Id) is selected from the group consisting of

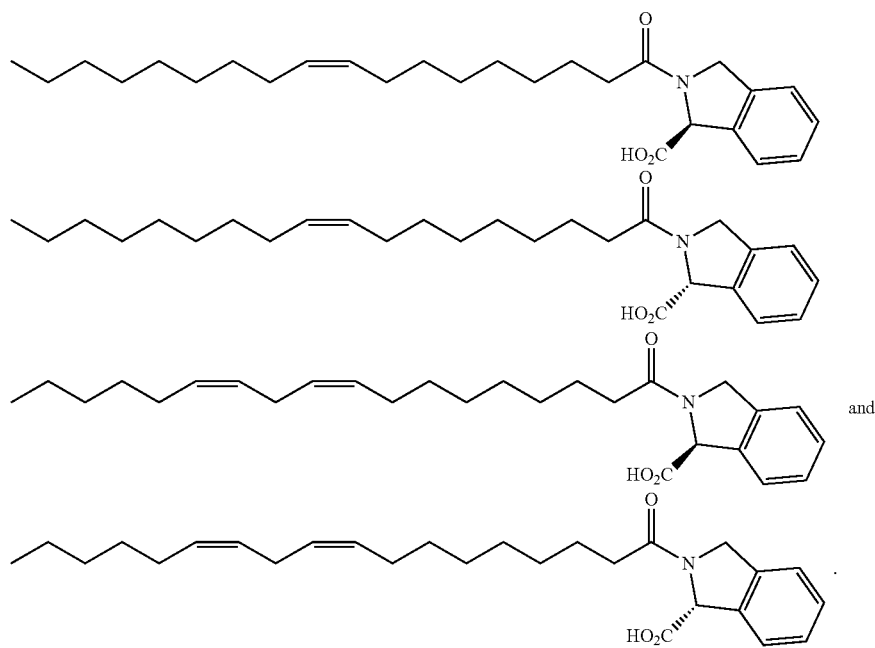

and

In some embodiments, the compound of Formula (Id) is

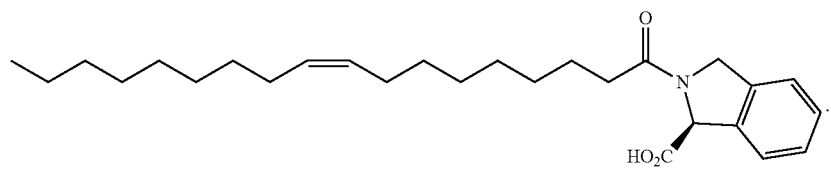 [SMILES: CCCCCCCC/C=C\CCCCCCCC(=O)N1Cc2ccccc2[C@H]1C(=O)O]

Methods of Treatment

Uncoupling of respiration can be stimulated by both proteins (e.g., UCP1) and small molecules, including chemical uncouplers. In some embodiments, the chemical uncoupler is an N-acyl amino acid (NAAs). When added to mitochondria, cells, or administered to a subject (e.g., a mouse), a chemical uncoupler can increase oxygen consumption. In mice, administration of NAAs produced an increase in energy expenditure, profound weight loss, and improvement of glycemia. Furthermore, NAAs are enzymatically regulated by the circulating enzyme PM20D1. In some embodiments, the chemical uncoupler is an NAA analog or an NAA derivative.

Accordingly, treatment of mice with these compounds may block PM20D1 activity, dysregulate endogenous N-acyl amino acids, and also cause anti-nociceptive behaviors. The disclosed compounds thus may useful for the treatment of a variety of pain conditions, including but not limited to neuropathic pain, osteoarthritis, dental pain, rheumatoid arthritis, cancer-associated pain, bone pain, nerve pain, lower back pain, and fibromyalgia.

In some embodiments, administration of a NAA or a NAA analog provides a novel therapeutic strategy for augmenting energy expenditure in humans to treat obesity and diabetes.

In one aspect, provided herein is a method of preventing or treating a metabolic disorder in a subject comprising administering to the subject a therapeutically effective amount of any one of the compounds disclosed herein. In some embodiments, the method of preventing or treating a metabolic disorder in a subject comprises administering to the subject a therapeutically effective amount of compound represented by Formula (I), or a pharmaceutically acceptable salt thereof:

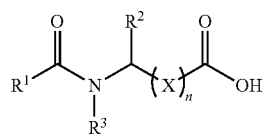

Formula (I)

wherein

X is —C(R$^3$)$_2$—, —N(R$^3$)—, —O—, —C(O)—, —C(O)O—, —OC(O)—, —C(O)N(R$^3$)—, or —N(R$^3$)C(O)—;

R$^1$ is (C$_{10}$-C$_{30}$)alkyl, (C$_{10}$-C$_{30}$)alkene, or (C$_{10}$-C$_{30}$)alkyne; wherein (C$_{10}$-C$_{30}$)alkyl, (C$_{10}$-C$_{30}$)alkene, or (C$_{10}$-C$_{30}$)alkyne is optionally substituted with one, two, three, or four substituents independently selected from the group consisting of (C$_1$-C$_6$)alkyl, (C$_1$-C$_6$)alkyloxy, cycloalkyl, and heterocycloalkyl;

R$^2$ is selected from the group consisting of H, (C$_1$-C$_6$)alkyl, (C$_1$-C$_6$)alkyloxy, cycloalkyl, heterocycloalkyl, aryl, heteroaryl, aralkyl, and heteroaralkyl, wherein (C$_1$-C$_6$)alkyl, (C$_1$-C$_6$)alkyloxy, cycloalkyl, heterocycloalkyl, aryl, heteroaryl, aralkyl, and heteroaralkyl is optionally substituted with one, two, three, or four substituents independently selected from the group consisting of halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and N(R$^3$)—C(=NH)—N(R$^3$)$_2$;

or

R$^2$ and —NR$^3$— taken together form a heterocycloalkyl or a heteroaryl, which is optionally substituted with one, two, three, or four substituents independently selected from the group consisting of halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and N(R$^3$)—C(=NH)—N(R$^3$)$_2$;

R$^3$ is H or (C$_1$-C$_6$)alkyl; and n is an integer from 0-5, thereby preventing or treating the metabolic disorder in the subject.

In some embodiments, provided herein is a method of preventing or treating a metabolic disorder in a subject comprising administering to the subject a therapeutically effective amount of a compound of Formula (I), Formula (Ia), Formula (Ib), Formula (Ic), Formula (Id), or a pharmaceutically acceptable salt thereof, thereby preventing or treating the metabolic disorder in the subject.

In some embodiments, the metabolic disorder is selected from the group consisting of pain, insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, and Prader-Labhart-Willi syndrome.

In some embodiments of the methods of preventing or treating a metabolic disorder, a compound of Formula (I), Formula (Ia), Formula (Ib), Formula (Ic), Formula (Id), or a pharmaceutically acceptable salt thereof, inhibits expression and/or activity of PM20D1.

In some embodiments of the methods of preventing or treating a metabolic disorder, the compound of Formula (I), Formula (Ia), Formula (Ib), Formula (Ic), Formula (Id), or a pharmaceutically acceptable salt thereof, is administered systemically.

In another aspect, provided herein is a method for modulating a metabolic response comprising contacting a cell with a NAA or a NAA analog, thereby modulating the metabolic response. In some embodiments, the method for modulating a metabolic response comprises contacting a cell with a compound of Formula (I), Formula (Ia), Formula (Ib), Formula (Ic), Formula (Id), or a pharmaceutically acceptable salt thereof, thereby modulating the metabolic response.

In some embodiments, the metabolic response is selected from the group consisting of:
a) modified thermogenesis in adipose cells;
b) modified differentiation of adipose cells;
c) modified insulin sensitivity of adipose cells;
d) modified basal respiration or uncoupled respiration;
e) modified whole body oxygen consumption;
f) modified obesity or appetite;
g) modified insulin secretion of pancreatic beta cells;
h) modified glucose tolerance;
i) modified expression of UCP1 protein;
j) modified N-lipidated amino acid amount and/or activity;
k) modified expression and/or activity of PM20D1;
l) modified brown fat and/or beige fat cell differentiation and/or activity; and
m) modified body weight.

In some embodiments, the metabolic response is upregulated.

In some embodiments, the metabolic response is downregulated.

In some embodiments, the metabolic response is inhibition of expression and/or activity of PM20D1.

In some embodiments, the metabolic response is uncoupled respiration.

In some embodiments, the metabolic response is inducing brown fat and/or beige fat cell differentiation and/or activity.

In some embodiments, the metabolic response is modified body weight. In some embodiments, the metabolic response is modified body weight, which is weight loss.

In some embodiments, a compound of Formula (I), Formula (Ia), Formula (Ib), Formula (Ic), Formula (Id), or a pharmaceutically acceptable salt thereof, inhibits expression and/or activity of PM20D1.

In some embodiments, a compound of Formula (I), Formula (Ia), Formula (Ib), Formula (Ic), Formula (Id), or a pharmaceutically acceptable salt thereof, is an uncoupler of mitochondrial respiration. In some embodiments, a compound of Formula (Id), or a pharmaceutically acceptable salt thereof, has exceptional uncoupling activity. In some embodiments, a compound of Formula (Id), or a pharmaceutically acceptable salt thereof, has superior uncoupling activity to a compound of Formula (Ib), Formula (Ic), or a pharmaceutically acceptable salt thereof.

In some embodiments, a compound of Formula (Id), or a pharmaceutically acceptable salt thereof, is completely resistant to the hydrolytic activity of PM20D1. In some embodiments, a compound of Formula (Ib), Formula (Ic), or a pharmaceutically acceptable salt thereof, is at least partially hydrolyzed by PM20D1. In some embodiments, a compound of Formula (Ib), Formula (Ic), or a pharmaceutically acceptable salt thereof, is at least partially inactivated by PM20D1. In some embodiments, a compound of Formula (Id), or a pharmaceutically acceptable salt thereof, has better pharmacokinetic properties compared to a compound of Formula (Ib), Formula (Ic), or a pharmaceutically acceptable salt thereof.

The methods of the present disclosure relate to the expression and/or activity of PM20D1 sufficient to modulate (e.g., induce or repress) brown and/or beige fat cell differentiation and/or activity, wherein increases in differentiated brown and/or beige fat cells or activity increase energy expenditure and favorably affect other metabolic processes and can therefore be used to treat metabolic disorders such as obesity, diabetes, decreased thermogenesis and subjects in need of more exercise; and, wherein decreases in differentiated brown and/or beige fat cells or activity decrease energy expenditure and can therefore be used to treat the effects of such conditions as cachexia, anorexia, and obesity-associated cancer.

The disclosure also relates to methods for increasing energy expenditure in a mammal comprising inducing expression and/or activity of PM20D1 sufficient to activate brown and/or beige fat cell differentiation or activity in the mammal, wherein the differentiated and/or more active brown fat and/or beige fat cells promote energy expenditure thereby increasing energy expenditure in the mammal.

The term "sufficient to activate" is intended to encompass any increase in expression and/or activity of PM20D1 that promotes, activates, stimulates, enhances, or results in brown fat and/or beige fat differentiation or activity.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular compound to treat a metabolic disorder can be monitored by comparing two or more samples obtained from a subject undergoing anti-metabolic disorder treatment or metabolic disorder-related disorder treatment. In general, it is preferable to obtain a first sample from the subject prior to beginning therapy and one or more samples during treatment. In such a use, cells from subjects with obesity or obesity-related disorders prior to therapy are examined and then changes in the cells from subjects with obesity or obesity-related disorders are monitored during the course of therapy. Alternatively, two or more successive samples obtained during treatment can be used without the need of a pre-treatment sample. In such a use, the first sample obtained from the subject is used for comparisons in subjects with obesity or obesity-related disorders.

Another aspect of the disclosure relates to a method for inducing brown fat and/or beige fat cell differentiation and/or activity in a mammal comprising administering to a mammal a compound disclosed herein and, optionally, monitoring the differentiation of brown fat cells in the mammal. Increased brown and/or beige adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by analyzing a) thermogenesis in adipose cells; b) differentiation of adipose cells; c) insulin sensitivity of adipose cells; d) basal respiration or uncoupled respiration; e) whole body oxygen consumption; f) obesity or appetite; g) insulin secretion of pancreatic beta cells; h) glucose tolerance; i) modified expression of UCP1 protein; and j) growth and effects of metabolic disorders, such as obesity-associated cancer, cachexia, anorexia, diabetes, and obesity.

In some embodiments of the methods disclosed herein, the subject is a mammal. In some embodiments, the subject is a non-human animal or a human. In some embodiments, the subject is a non-human animal. In some embodiments, the non-human animal is an animal model of the metabolic disorder. In some embodiments, the subject is a human.

Pharmaceutical Compositions

In another aspect, the present disclosure provides pharmaceutically acceptable compositions which comprise a therapeutically effective amount of a compound of Formula (I) that modulates (e.g., increases or decreases) PM20D1 expression and/or activity; and one or more pharmaceutically acceptable carriers (additives) and/or diluents.

As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of a compound of Formula (I) that modulates (e.g., inhibits) PM20D1 expression and/or activity, or expression and/or activity of a PM20D1 enzyme complex, or of NAAs, or composition comprising a compound of Formula (I) that modulates (e.g., inhibits) PM20D1 expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the compound of Formula (I) that modulates (e.g., inhibits) PM20D1 expression and/or activity, or expression and/or activity of the complex encompassed by the disclosure. These salts can be prepared in situ during the final isolation and purification of the a compound of Formula (I)s, or by separately reacting a purified a compound of Formula (I) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the compounds of Formula (I) useful in the methods of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a compound of Formula (I) that modulates (e.g., inhibits) PM20D1 expression and/or activity, or expression and/or activity of the complex. These salts can likewise be prepared in situ during the final isolation and purification of the compound of Formula (I), or by separately reacting the purified compound of Formula (I) in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present disclosure include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of Formula (I) that modulates (e.g., increases or decreases) PM20D1 expression and/or activity or expression and/or activity of natural or synthetic N-lipidated amino acids, with the carrier and, optionally, one or more accessory ingredients. In general, the formulations are prepared by uniformly and intimately bringing into association a compound of Formula (I) with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of Formula (I) as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound of Formula (I) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound of Formula (I).

Formulations which are suitable for vaginal administration also include pessaries, tampons, creams, gels, pastes, foams or spray formulations containing such carriers as are known in the art to be appropriate.

Dosage forms for the topical or transdermal administration of a compound of Formula (I) that modulates (e.g., increases or decreases) PM20D1 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a compound of Formula (I), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of Formula (I) that modulates (e.g., increases or decreases) PM20D1 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of Formula (I) that modulates (e.g., increases or decreases) PM20D1 expression and/or activity or expression and/or activity of natural or synthetic N-lipidated amino acids, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the compound of Formula (I) to shear, which can result in degradation of the compound.

Ordinarily, an aqueous aerosol is made by formulating an aqueous solution or suspension of the compound of Formula (I) together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of Formula (I) to the body. Such dosage forms can be made by dissolving or dispersing the compound of Formula (I) in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of Formula (I) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a compound of Formula (I) that modulates (e.g., increases or decreases) PM20D1 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the compounds of Formula (I) of the present disclosure are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this disclosure may be determined by the methods of the present disclosure so as to obtain an amount of the active ingredient, which is effective to achieve the desired therapeutic response for a particular subject, composition, and mode of administration, without being toxic to the subject.

EXEMPLIFICATION

Example 1: Chemical Synthesis

General Methods

All solvents and chemicals were reagent grade. Unless otherwise mentioned, all reagents and solvents were purchased from commercial vendors and used as received. Flash column chromatography was carried out on a Teledyne ISCO CombiFlash Rf system using prepacked columns. Solvents used include hexane, ethyl acetate (EtOAc), dichloromethane and methanol. Purity and characterization of compounds were established by a combination of HPLC, TLC, mass spectrometry, and NMR analyses. $^1$H and $^{13}$C NMR spectra were recorded on a Bruker Avance DPX-400 (400 MHz) spectrometer and were determined in chloroform-d or DMSO-d$^6$ with solvent peaks as the internal reference. Chemical shifts are reported in ppm relative to the reference signal, and coupling constant (J) values are reported in hertz (Hz). Thin layer chromatography (TLC) was performed on EMD precoated silica gel 60 F254 plates, and spots were visualized with UV light or iodine staining. Low resolution mass spectra were obtained using a Thermo Scientific ultimate 3000/LCQ Fleet system (ESI). High resolution mass spectra were obtained using a Thermo Scientific EXACTIVE system (ESI). All test compounds were greater than 95% pure as determined by NMR on a Bruker Avance DPX-400 (400 MHz) spectrometer.

Compounds were synthesized as depicted in Scheme 1 following well-known procedures. Commercial available acyl chloride 39, or converted from acid 38 with oxalyl chloride, coupled with corresponding natural or unnatural amino acid 40 to provide N acyl amino acid analogs 1-27 and 30-37 (Scheme 1). Oleoyl chloride reacted with ammonia hydroxide to give primary amide 41, which was reduced by LiAlH$_4$ to provide primary amine 42. Imidazole intermediate 43 was obtained by coupled amine 42 with CDI, which reacted with amino esters 44 in the presence of DIPEA. The resulted urea esters 45 were hydrolysis by LiOH to provide the desired urea analogs 28 or 29 in good yields (Scheme 2).

Scheme 1. Synthesis of Exemplary Chemical Uncouplers

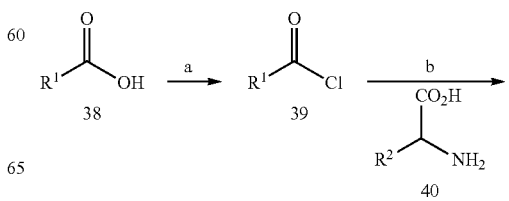

33

-continued

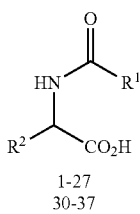

1-27
30-37

Reaction conditions: (a) oxalyl chloride, DMF, DCM; (b) NaOH, THF/H₂O.

General Procedure A.

To a mixture of amino acid (2 eq.) in acetone and water (0.1 M) was added K$_2$CO$_3$ (3 eq.) and acyl chloride (1 eq.) at 0° C. Then the reaction mixture was stirred at room temperature overnight before acidified by HCl (1 M) until pH<3. The mixture was extracted with ethyl estate, washed with brine. The combined organic layers were dried over anhydrous Na$_2$SO$_4$ and filtered. The filtrate was concentrated in vacuo, and the residue was purified by column chromatography (silica gel, ethyl acetate/hexanes) to give the desired product.

General Procedure B.

To a solution of fatty acid (1 eq.) in DCM was added with oxalyl chloride (1.2 eq.) and one drop of DMF at 0° C. Then the mixture was stirred at room temperature for 2 hours. The mixture was concentrated and dissolved in DCM, added to a suspension of amino acid (1.5 eq.) and DIPEA (2 eq.) in DCM. The reaction mixture was stirred at room temperature overnight before acidified by HCl (1.0 M) to pH<3. The result mixture was extracted with DCM, washed with brine, dried over anhydrous Na$_2$SO$_4$. Then the solvent was removed under reduced pressure. The residue was purified by flash chromatography on silica gel to give the product.

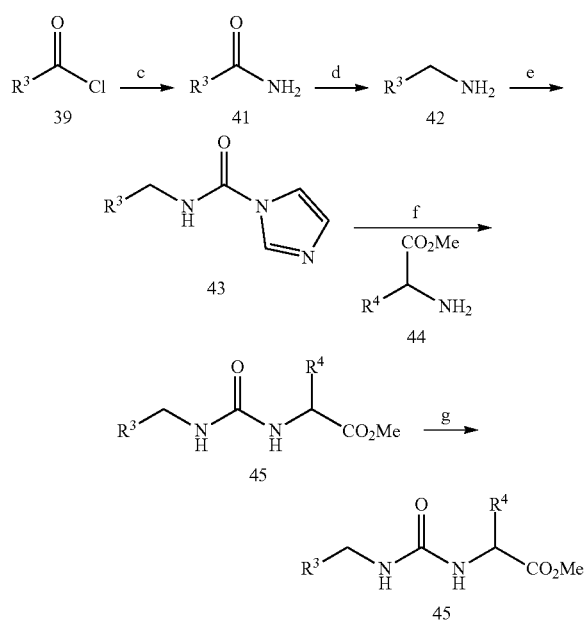

Scheme 2. Synthesis of Urea Analogs

Reaction conditions: (c) NH$_4$OH, THF; (d) LiAlH$_4$, THF; (e) CDI, DCM; (f) DIPEA, DCM; (g) LiOH, then HCl.

34

General Procedure C.

Step 1: To a solution of oleoyl chloride (1 g) in THF (20 mL) was added ammonia hydroxide (10 eq.) at 0° C. The mixture was stirred at room temperature for 3 hours. Then the mixture was filtered to give the desired oleamide 41 as a white solid (796 mg, 86%). Step 2: To a suspension of LiAlH$_4$ (2 eq.) in THF was added oleamide in one portion at 0° C. The mixture was heated to reflux overnight. Then the mixture was quenched with water (3 drops) at 0° C., added with 1 M NaOH solution, stirred at room temperature for 1 hour. The suspension was filtered through celite. The filtrate was diluted with EA, washed with water and brine, dried over anhydrous Na$_2$SO$_4$, filtered and concentrated to give (Z)-octadec-9-en-1-amine 42 (726 mg, 95%) which was used for the next step without further purification. Step 3: To a solution of (Z)-octadec-9-en-1-amine 42 in DMF was added DIEA (2 eq.) and CDI (1.5 eq.) at 0° C. Then the mix was stirred at room temperature overnight. The mixture was diluted with ethyl acetate, washed with NaHCO$_3$, brine, dried over anhydrous Na$_2$SO$_4$, filtered and concentrated, purified on silica gel to give (Z)—N-(octadec-9-en-1-yl)-1H-imidazole-1-carboxamide 43 (795 mg, 81%). Step 4: To a solution of (Z)—N-(octadec-9-en-1-yl)-1H-imidazole-1-carboxamide 43 in DMF was added DIEA (2 eq.) and amino ester 44. Then the mixture was stirred at room temperature overnight. Then the mixture was diluted with ethyl acetate, washed with NaHCO$_3$, brine, dried over anhydrous Na$_2$SO$_4$, filtered and concentrated, purified on silica gel to give intermediate 45 (75-80%). Step 5: To a solution of intermediate 45 in THF and H$_2$O (1:1) was added LiOH (5 eq.). Then the mixture was stirred at room temperature for 3 hours. The mixture was acidified with HCl (1M) until pH<3. Then the mixture was extracted with ethyl acetate, washed with brine, dried over anhydrous Na$_2$SO$_4$, filtered and concentrated to give the desired compound 28 or 29 (94-96%).

Example 1a

Oleoyl-L-phenylalanine (1)

Compound 1 was prepared from oleoyl chloride and L-phenyl alanine following the general procedure A as a white solid (1.3 g, 86%). $^1$H NMR (400 MHz, DMSO-d$^6$) δ 0.85 (t, J=5.0 Hz, 3H), 1.09-1.31 (m, 22H), 1.33-1.40 (m, 2H), 1.95-2.04 (m, 6H), 2.82 (dd, J=10.0, 13.8 Hz, 1H), 3.04 (dd, J=4.7, 13.4 Hz, 1H), 4.38-4.44 (m, 1H), 5.29-5.36 (m, 2H), 7.16-7.28 (m, 5H), 8.08 (d, J=8.0 Hz, 1H), 12.61 (brs, 1H). HRMS (ESI) m/z calcd for C$_{27}$H$_{44}$NO$_3$ [M+H]$^+$ 430.3316, found: 430.3317.

Example 1b

Oleoyl-D-phenylalanine (2)

Compound 2 was prepared from oleoyl chloride and D-phenyl alanine following the general procedure A as a white solid (35 mg, 88%). $^1$H NMR (400 MHz, CDCl$_3$) δ 0.89 (t, J=8.0 Hz, 3H), 1.20-1.43 (m, 22H), 1.53-1.62 (m, 2H), 1.95-2.08 (m, 4H), 2.19 (t, J=8.0 Hz, 2H), 3.11-3.28 (m, 2H), 4.86-4.91 (m, 1H), 5.32-5.42 (m, 2H), 5.92 (d, J=8.0 Hz, 1H), 7.16-7.34 (m, 5H). HRMS (ESI) m/z calcd for C$_{27}$H$_{44}$NO$_3$ [M+H]$^+$ 430.3316, found: 430.3309.

Example 1c

N-phenethyloleamide (3)

Compound 3 was prepared from oleoyl chloride and 2-phenylethan-1-amine following the general procedure A as a white solid (45 mg, 90%). $^1$H NMR (400 MHz, CDCl$_3$) δ 0.89 (t, J=8.0 Hz, 3H), 1.23-1.40 (m, 20H), 1.57-1.62 (m, 2H), 1.99-2.05 (m, 4H), 2.12 (t, J=8.0 Hz, 2H), 2.83 (t, J=4.7 Hz, 1H), 3.54 (dd, J=4.7, 13.4 Hz, 2H), 5.34-5.42 (m, 3H), 7.19-7.26 (m, 3H), 7.31-7.34 (m, 2H). HRMS (ESI) m/z calcd for C$_{26}$H$_{46}$NO [M+H]$^+$ 386.3417, found: 386.3415.

Example 1d

Oleoyl-L-leucine (4)

Compound 4 was prepared from oleoyl chloride and L-leucine following the general procedure A as a white solid (2.5 g, 83%). $^1$H NMR (400 MHz, CDCl$_3$) δ 0.88 (t, J=7.0 Hz, 3H), 0.95 (d, J=3.6 Hz, 3H), 0.97 (d, J=3.6 Hz, 3H), 1.27-1.37 (m, 20H), 1.56-1.77 (m, 5H), 1.98-2.06 (m, 4H), 2.22 (t, J=7.3 Hz, 2H), 4.58-4.64 (m, 1H), 5.31-5.39 (m, 2H), 5.86 (d, J=8.0 Hz, 1H). HRMS (ESI) m/z calcd for C$_{24}$H$_{46}$NO$_3$ [M+H]$^+$ 396.3472, found: 396.3478.

Example 1e

Oleoyl-L-isoleucine (5)

Compound 5 was prepared from oleoyl chloride and L-isoleucine following the general procedure A as a white solid (230 mg, 87%). $^1$H NMR (400 MHz, DMSO-d$^6$) δ 0.81-0.88 (m, 6H), 1.19-1.32 (m, 22H), 1.34-1.52 (m, 3H), 1.70-1.80 (m, 1H), 1.93-2.03 (m, 4H), 2.06-2.22 (m, 2H), 4.17 (dd, J=6.2, 8.4 Hz, 1H), 5.28-5.36 (m, 2H), 7.92 (d, J=8.4 Hz, 1H), 12.50 (brs, 1H). HRMS (ESI) m/z calcd for C$_{24}$H$_{46}$NO$_3$ [M+H]$^+$ 396.3472, found: 396.3474.

Example 1f

Oleoyl-L-glutamine (6)

Compound 6 was prepared from oleoyl chloride and L-glutamine following the general procedure A as a white solid (28 mg, 78%). $^1$H NMR (400 MHz, CDCl$_3$) δ 0.88 (t, J=6.7 Hz, 3H), 1.19-1.38 (m, 20H), 1.58-1.68 (m, 2H), 1.93-2.07 (m, 5H), 2.25 (d, J=7.6 Hz, 2H), 2.38-2.48 (m, 1H), 2.54-2.65 (m, 1H), 4.46 (dd, J=6.2, 12.0 Hz, 1H), 5.30-5.38 (m, 2H), 6.17 (brs, 1H), 6.48 (brs, 1H), 7.18 (d, J=6.2 Hz, 1H). HRMS (ESI) m/z calcd for C$_{23}$H$_{43}$N$_2$O$_4$ [M+H]$^+$ 411.3217, found: 411.3224.

Example 1g

Oleoyl-L-proline (7)

Compound 7 was prepared from oleoyl chloride and L-proline following the general procedure A as a white solid (27 mg, 76%). $^1$H NMR (400 MHz, CDCl$_3$) δ 0.89 (t, J=6.7 Hz, 3H), 1.19-1.38 (m, 20H), 1.64-1.72 (m, 2H), 1.90-2.10 (m, 6H), 2.37 (d, J=7.6 Hz, 2H), 2.50-2.56 (m, 1H), 3.43-3.48 (m, 1H), 3.56-3.60 (m, 1H), 4.63 (dd, J=6.2, 12.0 Hz, 1H), 5.30-5.38 (m, 2H). HRMS (ESI) m/z calcd for C$_{23}$H$_{42}$NO$_3$ [M+H]$^+$ 380.3159, found: 380.3143.

Example 1h

Oleoyl-L-tryptophan (8)

Compound 8 was prepared from oleoyl chloride and L-tryptophan following the general procedure A as a white solid (20 mg, 73%). $^1$H NMR (400 MHz, CDCl$_3$) δ 0.88 (t, J=6.7 Hz, 3H), 1.19-1.38 (m, 22H), 1.47-1.58 (m, 2H), 1.94-2.06 (m, 4H), 2.07-2.17 (m, 2H), 3.30-3.42 (m, 2H), 4.91-4.96 (m, 1H), 5.29-5.38 (m, 2H), 6.00 (d, J=7.4 Hz, 1H), 7.03 (d, J=3.5 Hz, 1H), 7.12 (t, J=8.0 Hz, 1H), 7.21 (t, J=8.0 Hz, 1H), 7.36 (d, J=8.1 Hz, 1H), 7.57 (d, J=8.1 Hz, 1H), 8.22 (brs, 1H). HRMS (ESI) m/z calcd for C$_{29}$H$_{45}$N$_2$O$_3$ [M+H]$^+$ 469.3425, found: 469.3433.

Example 1i

Oleoyl-L-lysine (9)

Compound 9 was prepared from oleoyl chloride and mono Boc protected L-lysine following the general procedure A, then de-boc with TFA as a white solid (15 mg, 71%). $^1$H NMR (400 MHz, CDC$_3$) δ 0.84 (t, J=6.7 Hz, 3H), 1.17-1.34 (m, 22H), 1.36-1.44 (m, 2H), 1.50-1.58 (m, 2H), 1.63-1.75 (m, 2H), 1.93-1.99 (m, 4H), 2.13-2.24 (m, 2H), 2.84-2.96 (m, 2H), 4.07 (dd, J=6.2, 12.0 Hz, 1H), 5.26-5.34 (m, 2H), 7.12 (d, J=6.6 Hz, 1H). HRMS (ESI) m/z calcd for C$_{24}$H$_{47}$N$_2$O$_3$ [M+H]$^+$ 411.3581, found: 411.3574.

Example 1j

Oleoyl-L-tyrosine (10)

Compound 10 was prepared from oleoyl chloride and L-tyrosine following the general procedure A as a white solid (23 mg, 70%). $^1$H NMR (400 MHz, CDCl$_3$) δ 0.87 (t, J=6.6 Hz, 3H), 1.19-1.38 (m, 22H), 1.47-1.58 (m, 2H), 1.94-2.04 (m, 4H), 2.07-2.17 (m, 3H), 2.96-3.10 (m, 2H), 4.75 (brs, 1H), 5.29-5.38 (m, 2H), 6.19 (brs, 1H), 6.69 (d, J=6.7 Hz, 2H), 6.95 (d, J=6.7 Hz, 2H). HRMS (ESI) m/z calcd for C$_{27}$H$_{44}$NO$_4$ [M+H]$^+$ 446.3265, found: 446.3270.

Example 1k

Oleoyl-L-glutamic acid (11)

Compound 11 was prepared from oleoyl chloride and L-glutamic acid following the general procedure A as a white solid (13 mg, 65%). $^1$H NMR (400 MHz, CDCl$_3$) δ 0.88 (t, J=6.7 Hz, 3H), 1.19-1.38 (m, 20H), 1.58-1.68 (m, 2H), 1.93-2.07 (m, 4H), 2.08-2.18 (m, 1H), 2.20-2.30 (m, 3H), 2.42-2.60 (m, 2H), 4.65 (dd, J=6.5, 13.6 Hz, 1H), 5.30-5.38 (m, 2H), 6.53 (d, J=7.2 Hz, 1H), 8.23 (brs, 2H). HRMS (ESI) m/z calcd for C$_{23}$H$_{42}$NO$_5$ [M+H]$^+$ 412.3057, found: 412.3064.

Example 1l

Oleoylglycylglycine (12)

Compound 12 was prepared from oleoyl chloride and 3-aminopropanoic acid following the general procedure A as a white solid (48 mg, 84%). $^1$H NMR (400 MHz, DMSO-d$^6$) δ 0.88 (t, J=8.0 Hz, 3H), 1.25-1.38 (m, 20H), 1.61-1.66 (m, 2H), 1.96-2.04 (m, 6H), 2.25 (t, J=8.0 Hz, 2H), 4.08 (d, J=4.0 Hz, 1H), 5.29-5.36 (m, 2H), 5.60 (dd, J=8.0, 4.0 Hz, 4H), 6.03 (brs, 1H). HRMS (ESI) m/z calcd for $C_{22}H_{41}N_2O_4$ [M+H]$^+$ 397.3061, found: 397.2142.

Example 1m

3-Oleamidopropanoic acid (13)

Compound 13 was prepared from oleoyl chloride and 3-aminopropanoic acid following the general procedure A as a white solid (48 mg, 84%). $^1$H NMR (400 MHz, DMSO-d$^6$) δ 0.85 (t, J=8.0 Hz, 3H), 1.19-1.32 (m, 20H), 1.42-1.49 (m, 2H), 1.96-2.04 (m, 6H), 2.34 (t, J=8.0 Hz, 2H), 3.22 (dd, J=12.0, 4.0 Hz, 1H), 5.29-5.36 (m, 2H), 7.82 (t, J=8.4 Hz, 1H). HRMS (ESI) m/z calcd for $C_{21}H_{40}NO_3$ [M+H]$^+$ 354.3003, found: 354.3000.

Example 1n

Dodecanoyl-L-phenylalanine (14)

Compound 14 was prepared from dodecanoyl chloride and L-phenyl alanine following the general procedure A as a white solid (45 mg, 89%). $^1$H NMR (400 MHz, DMSO-d$^6$) δ 0.86 (t, J=6.6 Hz, 3H), 1.08-1.31 (m, 16H), 1.34-1.41 (m, 2H), 2.02 (t, J=7.4 Hz, 2H), 2.83 (dd, J=10.2, 13.8 Hz, 1H), 3.05 (dd, J=4.6, 13.8 Hz, 1H), 4.38-4.44 (m, 1H), 7.17-7.28 (m, 5H), 8.08 (d, J=7.0 Hz, 1H), 12.65 (brs, 1H). HRMS (ESI) m/z calcd for $C_{21}H_{34}NO_3$ [M+H]$^+$ 348.2533, found: 348.2544.

Example 1o

Palmitoyl-L-phenylalanine (15)

Compound 15 was prepared from palmitoyl chloride and L-phenyl alanine following the general procedure A as a white solid (36 mg, 89%). $^1$H NMR (400 MHz, DMSO-d$^6$) δ 0.85 (t, J=6.7 Hz, 3H), 1.08-1.31 (m, 24H), 1.35-1.40 (m, 2H), 2.02 (t, J=7.3 Hz, 2H), 2.83 (dd, J=10.0, 13.8 Hz, 1H), 3.04 (dd, J=4.7, 13.8 Hz, 1H), 4.38-4.44 (m, 1H), 7.17-7.28 (m, 5H), 8.08 (d, J=8.2 Hz, 1H), 12.63 (brs, 1H). HRMS (ESI) m/z calcd for $C_{25}H_{42}NO_3$ [M+H]$^+$ 404.3159, found: 404.3159.

Example 1p

Stearoyl-L-phenylalanine (16)

Compound 16 was prepared from stearoyl chloride and L-phenyl alanine following the general procedure A as a white solid (36 mg, 89%). $^1$H NMR (400 MHz, DMSO-d$^6$) δ 0.85 (t, J=6.7 Hz, 3H), 1.08-1.31 (m, 28H), 1.33-1.40 (m, 2H), 2.01 (t, J=7.3 Hz, 2H), 2.82 (dd, J=10.0, 13.8 Hz, 1H), 3.04 (dd, J=4.7, 13.8 Hz, 1H), 4.38-4.44 (m, 1H), 7.16-7.28 (m, 5H), 8.09 (d, J=8.2 Hz, 1H), 12.63 (brs, 1H). HRMS (ESI) m/z calcd for $C_{27}H_{46}NO_3$ [M+H]$^+$ 432.3472, found: 432.3477.

Example 1q

Icosanoyl-L-phenylalanine (17). Compound 17 was prepared from icosanoyl chloride and L-phenyl alanine following the general procedure A as a white solid (51 mg, 87%). $^1$H NMR (400 MHz, DMSO-d$^6$) δ 0.86 (t, J=5.0 Hz, 3H), 1.09-1.31 (m, 32H), 1.33-1.40 (m, 2H), 2.02 (t, J=7.3 Hz, 2H), 2.83 (dd, J=10.2, 13.8 Hz, 1H), 3.05 (dd, J=5.3, 14.2 Hz, 1H), 4.38-4.44 (m, 1H), 7.17-7.28 (m, 5H), 8.08 (d, J=8.0 Hz, 1H), 12.97 (brs, 1H). HRMS (ESI) m/z calcd for $C_{29}H_{50}NO_3$ [M+H]$^+$ 460.3785, found: 460.3796.

Example 1r

Docosanoyl-L-phenylalanine (18). Compound 18 was prepared from docosanoic acid and L-phenyl alanine following the general procedure B as a white solid (5 mg, 65%). $^1$H NMR (400 MHz, DMSO-d$^6$) δ 0.77-0.87 (m, 9H), 1.08-1.42 (m, 22H), 1.43-1.53 (m, 2H), 1.72-1.85 (m, 1H), 1.95-2.02 (m, 4H), 2.06-2.21 (m, 2H), 4.17 (dd, J=6.2, 8.5 Hz, 1H), 5.28-5.36 (m, 2H), 7.91 (d, J=8.5 Hz, 1H), 12.50 (brs, 1H). HRMS (ESI) m/z calcd for $C_{31}H_{54}NO_3$ [M+H]$^+$ 488.4098, found: 488.4071.

Example 1s ((9Z,12Z)-Octadeca-9,12-dienoyl)-L-phenylalanine (19)

Compound 19 was prepared from linoleic acid and L-phenyl alanine following the general procedure B as a white solid (35 mg, 75%). $^1$H NMR (400 MHz, DMSO-d$^6$) δ 0.86 (t, J=6.7 Hz, 3H), 0.98-1.40 (m, 16H), 1.99-2.04 (m, 6H), 2.74 (t, J=6.1 Hz, 3H), 2.86 (dd, J=7.4, 13.4 Hz, 1H), 3.06 (dd, J=4.9, 13.4 Hz, 1H), 4.13-4.18 (m, 1H), 5.28-5.38 (m, 4H), 7.10-7.21 (m, 5H), 7.42 (d, J=8.0 Hz, 1H). HRMS (ESI) m/z calcd for $C_{27}H_{42}NO_3$ [M+H]$^+$ 428.3159, found: 428.3174.

Example 1t ((8Z,11Z,14Z)-Octadeca-8,11,14-trienoyl)-L-phenylalanine (20)

Compound 20 was prepared from (8Z,11Z,14Z)-octadeca-8,11,14-trienoic acid and L-phenyl alanine following the general procedure B as a white solid (13 mg, 70%). $^1$H NMR (400 MHz, CDCl$_3$) δ 0.90 (t, J=7.5 Hz, 3H), 2.01-2.31 (m, 6H), 1.99-2.04 (m, 6H), 2.77-2.86 (m, 10H), 3.06-3.13 (m, 1H), 3.21-3.29 (m, 1H), 4.70-4.81 (m, 1H), 5.30-5.44 (m, 6H), 5.94 (d, J=8.0 Hz, 1H), 7.16-7.33 (m, 5H). HRMS (ESI) m/z calcd for $C_{27}H_{40}NO_3$ [M+H]$^+$ 426.3003, found: 426.3929.

Example 1u (E)-Octadec-9-enoyl-L-phenylalanine (21)

Compound 21 was prepared from (E)-octadec-9-enoic acid and L-phenyl alanine following the general procedure B as a white solid (67 mg, 80%). $^1$H NMR (400 MHz, CDC$_3$) δ 0.89 (t, J=7.5 Hz, 3H), 1.20-1.38 (m, 22H), 1.52-1.62 (m, 2H), 1.92-2.01 (m, 4H), 2.15-2.20 (m, 2H), 3.10-3.29 (m, 2H), 4.87 (dd, J=7.4, 13.4 Hz, 1H), 5.36-5.44 (m, 2H), 5.96 (d, J=8.0 Hz, 1H), 7.16-7.33 (m, 5H). HRMS (ESI) m/z calcd for $C_{27}H_{44}NO_3$ [M+H]$^+$ 430.3316, found: 430.3293.

Example 1v (Z)-Octadec-6-enoyl-L-phenylalanine (22)

Compound 22 was prepared from (Z)-octadec-6-enoic acid and L-phenyl alanine following the general procedure B as a white solid (31 mg, 75%). $^1$H NMR (400 MHz, CDC$_3$) δ 0.89 (t, J=7.5 Hz, 3H), 1.20-1.38 (m, 22H), 1.54-1.65 (m, 2H), 1.98-2.04 (m, 4H), 2.17-2.27 (m, 2H), 3.10-3.29 (m, 2H), 4.90 (dd, J=7.4, 13.4 Hz, 1H), 5.27-5.41 (m, 2H), 6.03 (d, J=7.4 Hz, 1H), 7.16-7.33 (m, 5H). HRMS (ESI) m/z calcd for $C_{27}H_{44}NO_3$ [M+H]$^+$ 430.3316, found: 430.3294.

Example 1w (Z)-Octadec-11-enoyl-L-phenylalanine (23)

Compound 23 was prepared from (Z)-octadec-11-enoic acid and L-phenyl alanine following the general procedure B as a white solid (35 mg, 77%). $^1$H NMR (400 MHz, $CDC_3$) δ 0.89 (t, J=7.5 Hz, 3H), 1.20-1.38 (m, 22H), 1.54-1.65 (m, 2H), 1.98-2.04 (m, 4H), 2.17-2.27 (m, 2H), 3.11-3.29 (m, 2H), 4.89 (dd, J=7.4, 13.4 Hz, 1H), 5.30-5.41 (m, 2H), 6.03 (d, J=7.4 Hz, 1H), 7.16-7.33 (m, 5H). HRMS (ESI) m/z calcd for $C_{27}H_{44}NO_3$ [M+H]$^+$ 430.3316, found: 430.3295.

Example 1x (Z)-Icos-11-enoyl-L-phenylalanine (24)

Compound 24 was prepared from (Z)-icos-11-enoic acid and L-phenyl alanine following the general procedure B as a white solid (30 mg, 73%). $^1$H NMR (400 MHz, CDCl$_3$) δ 0.89 (t, J=7.5 Hz, 3H), 1.20-1.38 (m, 26H), 1.54-1.65 (m, 2H), 1.98-2.04 (m, 4H), 2.17-2.27 (m, 2H), 3.11-3.28 (m, 2H), 4.90 (dd, J=7.4, 13.4 Hz, 1H), 5.30-5.41 (m, 2H), 5.99 (d, J=7.4 Hz, 1H), 7.16-7.33 (m, 5H). HRMS (ESI) m/z calcd for $C_{29}H_{48}NO_3$ [M+H]$^+$ 458.3629, found: 458.3613.

Example 1v ((5Z,8Z,11Z,14Z)-Icosa-5,8,11,14-tetraenoyl)-L-phenylalanine (25)

Compound 25 was prepared from (5Z,8Z,11Z,14Z)-icosa-5,8,11,14-tetraenoic acid and L-phenyl alanine following the general procedure B as a white solid (10 mg, 71%). $^1$H NMR (400 MHz, CDCl$_3$) δ 0.89 (t, J=7.5 Hz, 3H), 1.20-1.38 (m, 4H), 1.64-1.70 (m, 2H), 2.02-2.09 (m, 6H), 2.16-2.20 (m, 2H), 2.76-2.84 (m, 6H), 3.11-3.28 (m, 2H), 4.86 (dd, J=7.4, 13.4 Hz, 1H), 5.25-5.41 (m, 8H), 5.82 (d, J=7.4 Hz, 1H), 7.16-7.33 (m, 5H). HRMS (ESI) m/z calcd for $C_{29}H_{42}NO_3$ [M+H]$^+$ 452.3159, found: 452.3341.

Example 1z ((5Z,8Z,11Z,14Z,17Z)-Icosa-5,8,11,14,17-pentaenoyl)-L-phenylalanine (26)

Compound 26 was prepared from (5Z,8Z,11Z,14Z,17Z)-icosa-5,8,11,14,17-pentaenoic acid and L-phenyl alanine following the general procedure B as a white solid (10 mg, 71%). $^1$H NMR (400 MHz, CDCl$_3$) δ 0.98 (t, J=7.5 Hz, 3H), 1.60-1.67 (m, 2H), 2.01-2.17 (m, 6H), 2.76-2.84 (m, 8H), 3.09-3.26 (m, 2H), 4.82 (dd, J=7.4, 13.4 Hz, 1H), 5.25-5.41 (m, 10H), 6.02 (d, J=7.4 Hz, 1H), 7.16-7.33 (m, 5H). HRMS (ESI) m/z calcd for $C_{29}H_{40}NO_3$ [M+H]$^+$ 450.3003, found: 450.2979.

Example 1aa ((4Z,7Z,10Z,13Z,16Z,19Z)-Docosa-4,7,10,13,16,19-hexaenoyl)-L-phenylalanine (27)

Compound 27 was prepared from docosahexaenoic acid and L-phenyl alanine following the general procedure B as a white solid (5 mg, 65%) $^1$H NMR (400 MHz, CDC$_3$) δ 0.97 (t, J=7.5 Hz, 3H), 1.22-1.40 (m, 10H) 1.52-1.62 (m, 2H), 2.02-2.09 (m, 4H), 2.19 (t, J=6.0 Hz, 1H), 2.81 (t, J=8.0 Hz, 4H), 3.11-3.29 (m, 2H), 4.89 (dd, J=8.0, 16 Hz, 1H), 5.22-5.44 (m, 12H), 5.98-6.10 (m, 1H), 7.10-7.24 (m, 5H). HRMS (ESI) m/z calcd for $C_{31}H_{40}NO_3Na$ [M+Na]$^+$ 498.2979, found: 498.2979.

Example 1bb (Z)-(Octadec-9-en-1-ylcarbamoyl)glycine (28)

Compound 28 was prepared from intermediate 43 and glycine methyl ester following the general procedure C as a white solid (5 mg, 94%). $^1$H NMR (400 MHz, CDCl$_3$) δ 0.89 (t, J=7.5 Hz, 3H), 1.20-1.38 (m, 22H), 1.59-1.67 (m, 2H), 1.97-2.06 (m, 4H), 2.34-2.38 (m, 1H), 3.13-3.21 (m, 1H), 3.47-3.54 (m, 2H), 3.95-4.05 (m, 1H), 5.32-5.38 (m, 2H). HRMS (ESI) m/z calcd for $C_{21}H_{41}N_2O_3$ [M+H]$^+$ 369.3112, found: 369.3098.

Example 1cc (Z)-(Octadec-9-en-1-ylcarbamoyl)-L-phenylalanine (29)

Compound 29 was prepared from intermediate 43 and L-phenyl alanine methyl ester following the general procedure C as a white solid (9 mg, 96%). $^1$H NMR (400 MHz, CDC$_3$) δ 0.89 (t, J=7.5 Hz, 3H), 1.20-1.38 (m, 22H), 1.43-1.51 (m, 2H), 1.95-2.06 (m, 4H), 2.84-2.90 (m, 1H), 3.24-3.29 (m, 1H), 3.36-3.46 (m, 2H), 4.22-4.25 (m, 1H), 5.31-5.38 (m, 2H), 5.62 (brs, 1H), 7.19-7.35 (m, 5H). HRMS (ESI) m/z calcd for $C_{28}H_{47}N_2O_3$ [M+H]$^+$ 459.3581, found: 459.3554.

Example 1dd (S)-1-Oleoylpiperidine-2-carboxylic acid (30)

Compound 30 was prepared from oleoyl chloride and (S)-piperidine-2-carboxylic acid following the general procedure A as a white solid (35 mg, 82%). $^1$H NMR (400 MHz, CDC$_3$) δ 0.81 (t, J=8.0 Hz, 3H), 1.09-1.31 (m, 20H), 1.43-1.51 (m, 2H), 1.63-1.70 (m, 4H), 1.86-2.01 (m, 4H), 2.22-2.23 (m, 2H), 2.26-2.33 (m, 2H), 3.13-3.20 (m, 2H), 3.68-3.72 (m, 2H), 4.48-4.53 (m, 1H), 5.24-5.33 (m, 2H). HRMS (ESI) m/z calcd for $C_{24}H_{44}NO_3$ [M+H]$^+$ 394.3316, found: 394.3298.

Example 1ee (S)-2-Oleoyl-1,2,3,4-tetrahydroisoquinoline-3-carboxylic acid (31)

Compound 31 was prepared from oleoyl chloride and (S)-1,2,3,4-tetrahydroisoquinoline-3-carboxylic acid following the general procedure A as a white solid (25 mg, 78%). $^1$H NMR (400 MHz, CDCl$_3$) δ 0.90 (t, J=8.0 Hz, 3H), 1.09-1.31 (m, 22H), 1.63-1.70 (m, 2H), 2.01-2.08 (m, 4H), 2.46-2.51 (m, 2H), 3.09-3.15 (m, 1H), 3.27-3.38 (m, 1H), 4.61-4.71 (m, 2H), 5.35-5.42 (m, 2H), 7.12-7.26 (m, 4H). HRMS (ESI) m/z calcd for $C_{28}H_{44}NO_3$ [M+H]$^+$ 442.3316, found: 442.3292.

Example 1ff

2-Oleoyl-1,2,3,4-tetrahydroisoquinoline-1-carboxylic acid (32)

Compound 32 was prepared from oleoyl chloride and 1,2,3,4-tetrahydroisoquinoline-1-carboxylic acid following the general procedure A as a white solid (40 mg, 86%). $^1$H NMR (400 MHz, CDC$_3$) δ 0.90 (t, J=8.0 Hz, 3H), 1.09-1.31 (m, 22H), 1.63-1.70 (m, 2H), 2.01-2.08 (m, 4H), 2.46-2.51 (m, 2H), 3.09-3.15 (m, 1H), 3.27-3.38 (m, 1H), 4.61-4.71 (m, 2H), 5.35-5.42 (m, 2H), 7.12-7.26 (m, 4H). HRMS (ESI) m/z calcd for C$_{28}$H$_{44}$NO$_3$ [M+H]$^+$ 442.3316, found: 442.3291.

Example 1gg (S)-2-Oleoylisoindoline-1-carboxylic acid (33)

Compound 33 was prepared from oleoyl chloride and (S)-isoindoline-1-carboxylic acid following the general procedure A as a white solid (1.1 g, 81%). $^1$H NMR (400 MHz, CDC$_3$) δ 0.88 (t, J=8.0 Hz, 3H), 1.09-1.47 (m, 22H), 1.64-1.76 (m, 2H), 1.94-2.08 (m, 4H), 2.26-2.51 (m, 2H), 3.09-3.15 (m, 1H), 4.78-4.96 (m, 2H), 5.30-5.42 (m, 2H), 5.69 (s, 1H), 7.26-7.52 (m, 4H), 9.16 (brs, 1H). $^{13}$C NMR (100 MHz, CDCl$_3$) δ 173.5, 173.0, 136.5, 134.3, 130.0, 129.8, 128.9, 128.3, 123.8, 122.7, 65.1, 52.7, 34.2, 31.9, 29.8, 29.7, 29.5, 29.3, 29.2, 27.2, 24.5, 22.7, 14.1. HRMS (ESI) m/z calcd for C$_{27}$H$_{44}$NO$_3$ [M+H]$^+$ 428.3159, found: 428.3136.

Example 1hh (R)-2-Oleoylisoindoline-1-carboxylic acid (34)

Compound 34 was prepared from oleoyl chloride and (R)-isoindoline-1-carboxylic acid following the general procedure A as a white solid (45 mg, 73%). $^1$H NMR (400 MHz, CDC$_3$) δ 0.89 (t, J=8.0 Hz, 3H), 1.21-1.44 (m, 22H), 1.68-1.76 (m, 2H), 1.96-2.08 (m, 4H), 2.45-2.51 (m, 2H), 3.09-3.15 (m, 1H), 4.78-4.96 (m, 2H), 5.30-5.42 (m, 2H), 5.75 (s, 1H), 7.26-7.52 (m, 4H). HRMS (ESI) m/z calcd for C$_{27}$H$_{44}$NO$_3$ [M+H]$^+$ 428.3159, found: 428.3141.

Example 1ii (S)-1-Oleoylindoline-2-carboxylic acid (35)

Compound 35 was prepared from oleoyl chloride and (S)-indoline-2-carboxylic acid following the general procedure A as a white solid (37 mg, 77%). $^1$H NMR (400 MHz, CDC$_3$) δ 0.89 (t, J=8.0 Hz, 3H), 1.22-1.45 (m, 22H), 1.68-1.82 (m, 2H), 1.96-2.08 (m, 4H), 2.29-2.42 (m, 1H), 2.66-2.80 (m, 1H), 3.28-3.33 (m, 1H), 3.41-3.67 (m, 1H), 4.93-5.21 (m, 1H), 5.30-5.42 (m, 2H), 7.01-7.26 (m, 4H). HRMS (ESI) m/z calcd for C$_{27}$H$_{44}$NO$_3$ [M+H]$^+$ 428.3159, found: 428.3142.

Example 1jj (S)-2-((9Z,12Z)-Octadeca-9,12-dienoyl)isoindoline-1-carboxylic acid (36)

Compound 36 was prepared from linoleic acid and (S)-isoindoline-1-carboxylic acid following the general procedure B as a white solid (35 mg, 75%). $^1$H NMR (400 MHz, CDC$_3$) δ 0.89 (t, J=8.0 Hz, 3H), 1.17-1.43 (m, 18H), 1.56-1.75 (m, 2H), 1.98-2.10 (m, 4H), 2.25-2.49 (m, 2H), 2.74-2.81 (m, 2H), 4.81-4.97 (m, 2H), 5.30-5.42 (m, 2H), 5.72 (s, 1H), 7.27-7.55 (m, 4H). HRMS (ESI) m/z calcd for C$_{27}$H$_{40}$NO$_3$ [M+H]$^+$ 426.3003, found: 426.2982.

Example 1kk (R)-2-((9Z,12Z)-Octadeca-9,12-dienoyl)isoindoline-1-carboxylic acid (37)

Compound 37 was prepared from linoleic acid and (R)-isoindoline-1-carboxylic acid following the general procedure B as a white solid (1.2 g, 74%). $^1$H NMR (400 MHz, CDCl$_3$) δ 0.89 (t, J=8.0 Hz, 3H), 1.23-1.43 (m, 18H), 1.67-1.75 (m, 2H), 2.00-2.10 (m, 4H), 2.25-2.49 (m, 2H), 2.74-2.81 (m, 2H), 4.81-4.97 (m, 2H), 5.30-5.42 (m, 2H), 5.72 (s, 1H), 7.27-7.55 (m, 4H). $^{13}$C NMR (100 MHz, CDC$_3$) δ 173.5, 173.2, 136.5, 134.3, 130.2, 130.1, 128.9, 128.0, 127.9, 123.8, 122.7, 65.0, 52.7, 34.2, 31.5, 29.6, 29.4, 29.3, 29.2, 27.2, 25.7, 24.5, 22.6, 14.1. HRMS (ESI) m/z calcd for C$_{27}$H$_{40}$NO$_3$ [M+H]$^+$ 426.3003, found: 426.2981.

Example 2: In Vitro Biological Studies

Measurement of Cellular Respiration

Oligomycin was purchased from EMD Millipore, and FCCP and rotenone were purchased from Sigma. C2C12 cells were seeded at 35,000 cells/well in an XF24 cell culture microplate (V7-PS, Seahorse Bioscience) and analyzed the following day. On the day of analysis, the cells were washed once with Seahorse respiration buffer (8.3 g/l DMEM, 1.8 g/l NaCl, 1 mM pyruvate, 20 mM glucose, pen/strep), placed in 0.5 ml Seahorse respiration buffer, and incubated in a CO$_2$-free incubator for 1 h. Port injection solutions were prepared as follows (final concentrations in assay in parentheses): 10 μM oligomycin (1 μM final), 500 μM indicated compound (50 μM final), 2 μM FCCP (0.2 μM final), and 30 μM rotenone (3 μM final). The Seahorse program was run as follows: basal measurement, 3 cycles; inject port A (oligomycin), 3 cycles; inject port B (compounds), 8 cycles; inject port C (FCCP), 3 cycles; inject port D (rotenone), 3 cycles. Each cycle consisted of mix 2 min, wait 0 min, and measure 2 min. For data expressed as a percentage of oligomycin-treated basal, the respiration at cycle 6 was normalized to 100%, and the maximum respiration at any time point between cycles 7 and 15 inclusive was used.

Generation of Recombinant PM20D1

Three 10 cm plates of 293T cells were transiently transfected with murine PM20D1-6xHis-Flag plasmid (Addgene plasmid #84566) using PolyFect according to the manufacturer's instructions. After 48 h, cells were washed twice in PBS and switched to serum free DMEM with penicillin and streptomycin. Serum free conditioned media was collected 24 h later and concentrated ~10-fold in 30 kDa MWCO filters (EMD Millipore) according to the manufacturer's instructions. The concentrated media was centrifuged to remove debris (600×g, 10 min, 4° C.) and the supernatant containing PM20D1-flag was decanted into a new tube. PM20D1-flag was immunoaffinity purified overnight at 4° C. from the concentrated media using magnetic Flag-M2 beads (Sigma Aldrich). The beads were collected, washed three times in PBS, eluted with 3× Flag peptide (0.1 μg/ml in PBS, Sigma Aldrich), aliquoted, and stored at −80° C.

PM20D1 Hydrolysis Assays

Figure 2:
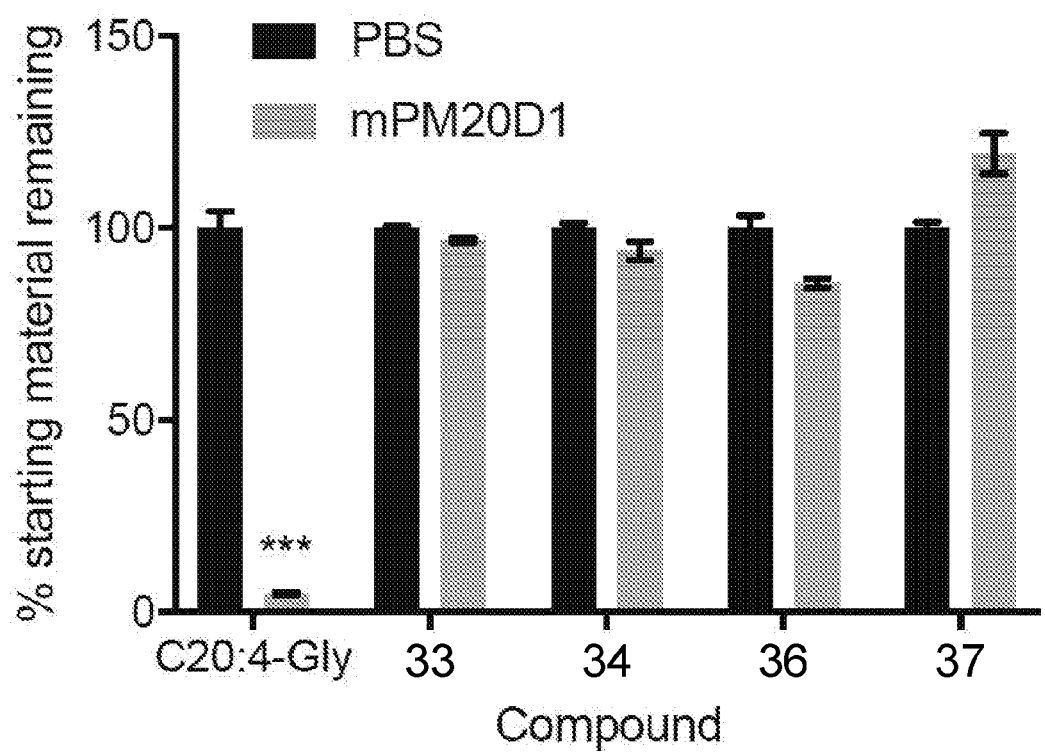
FIG. 2 shows hydrolysis by PM20D1 of exemplary compounds of the disclosure.

Some of the chemical uncouplers of the disclosure are entirely resistant to hydrolysis by PM20D1 (e.g., compounds 33, 34, 36, and 37; FIG. 2).

10 nmol of the indicated compound was incubated in 100 µl PBS (100 VM initial substrate). Reactions were initiated by the addition of PBS or mPM20D1 (5 µl). After 1 h at 37° C., reactions were quenched with 600 of a 2:1 v/v mixture of chloroform and methanol with 10 nmol $d_{31}$-palmitate as an internal standard. The reactions were vortexed and the organic layer was transferred to a sample vial for analysis by LC-MS. For separation of polar metabolites, normal-phase chromatography was performed with a Luna-5 mm $NH_2$ column (50 mm×4.60 mm, Phenomenex). Mobile phases were as follows: Buffer A, acetonitrile; Buffer B, 95:5 water/acetonitrile with 0.1% formic acid or 0.2% ammonium hydroxide with 50 mM ammonium acetate for positive and negative ionization mode, respectively. The flow rate for each run started at 0.2 ml/min for 2 min, followed by a gradient starting at 0% B and increasing linearly to 100% B over the course of 15 min with a flow rate of 0.7 ml/min, followed by an isocratic gradient of 100% B for 10 min at 0.7 ml/min before equilibrating for 5 min at 0% B with a flow rate of 0.7 ml/min. MS analysis was performed with an electrospray ionization (ESI) source on an Agilent 6430 QQQ LC-MS/MS. The capillary voltage was set to 3.5 kV, and the fragmentor voltage was set to 100 V. The drying gas temperature was 325° C., the drying gas flow rate was 10 l/min, and the nebulizer pressure was 45 psi. Monitoring of hydrolysis starting materials and products was performed by scanning a mass range of m/z 50-1200. Peaks corresponding to the liberated fatty acids (products) or the intact starting material was integrated.

Liver Microsome Stability Assays

Figure 3:
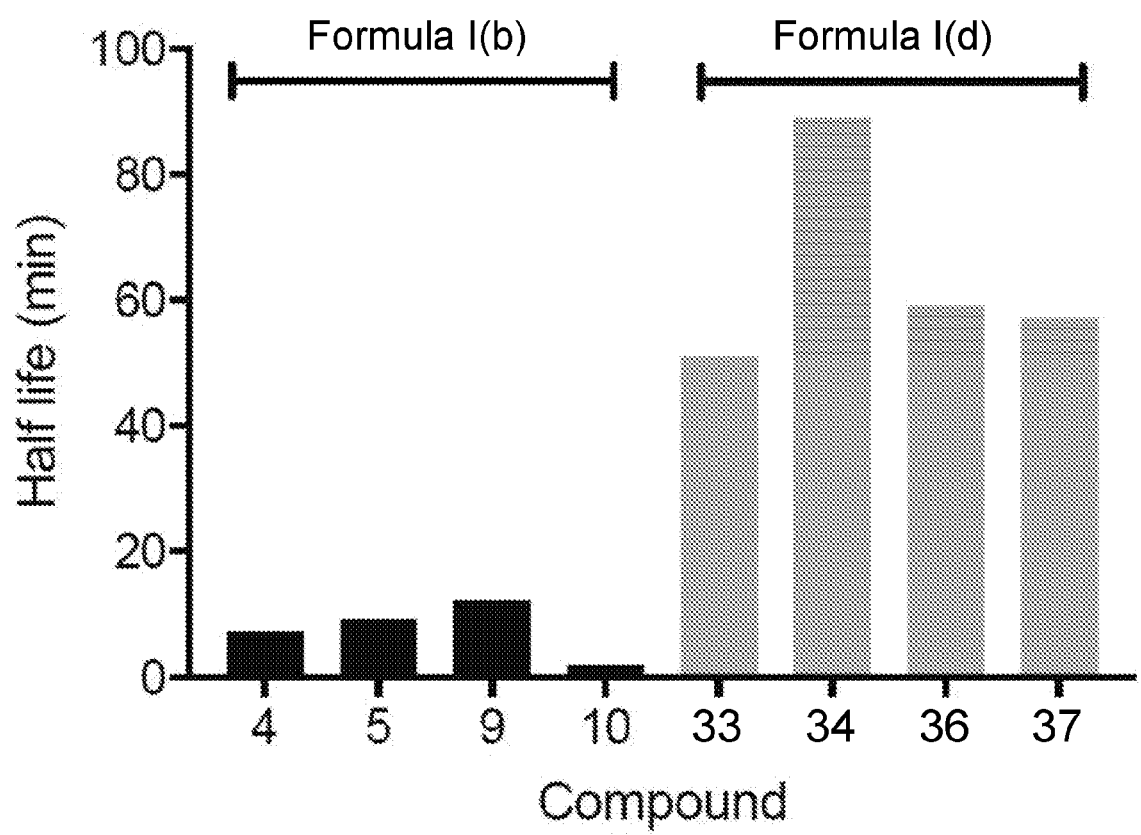
FIG. 3 shows microsome stability of exemplary compounds of the disclosure.

Some of the chemical uncouplers of the disclosure have long in vitro half-lives (e.g., compounds 33, 34, 36, and 37; FIG. 3). The compounds were evaluated in a mouse liver microsome assay.

Microsome stability was evaluated by incubating 1 µM test compound with 1 mg/mL hepatic microsomes in 100 mM KPi, pH 7.4 at 37 C with shaking. The reaction was initiated by adding NADPH (1 mM final concentration). Aliquots were removed at 0, 5, 10, 20, 40, and 60 minutes and added to acetonitrile (5× v:v) to stop the reaction and precipitate the protein. NADPH dependence of the reaction was evaluated with -NADPH samples. At the end of the assay, the samples were centrifuged through a Millipore Multiscreen Solvinter 0.45 micron low binding PTFE hydrophilic filter plate and analyzed by LC-MS/MS. Data is log transformed and represented as half-life.

Example 3: Exemplary Uncoupling Bioactivity

Tables 1-4 show uncoupling bioactivity of compounds of the disclosure with different fatty acid side chains. Respiration in C2C12 cells is shown as maximal increases versus basal oligomycin-treated respiration, which is normalized to 100%. Data are shown as means SEM, n=3-6/group.

Uncoupling bioactivity for exemplary chemical uncouplers of the disclosure with various head groups is provided below in Table 2.

TABLE 2

Structures and uncoupling bioactivity for exemplary chemical uncouplers with various head groups.

| Compound | Head group name | R = | % stimulation of respiration (baseline = 100%) |
|---|---|---|---|
| 1 | L-Phe | (L-Phe structure with Ph, $CO_2H$, NH) | 161 ± 12 |
| 2 | D-Phe | (D-Phe structure with Ph, $CO_2H$, NH) | 173 ± 9 |
| 3 | n/a | (structure with Ph, NH) | 104 ± 4 |
| 4 | L-Leu | (L-Leu structure with $CO_2H$, NH) | 178 ± 13 |

TABLE 2-continued

Structures and uncoupling bioactivity for exemplary chemical uncouplers with various head groups.

| Compound | Head group name | R = | % stimulation of respiration (baseline = 100%) |
|---|---|---|---|
| 5 | L-Ile | | 167 ± 14 |
| 6 | L-Gln | | 164 ± 4 |
| 7 | L-Pro | | 182 ± 7 |
| 8 | L-Trp | | 147 ± 9 |
| 9 | L-Lys | | 108 ± 4 |
| 10 | L-Tyr | | 105 ± 13 |
| 11 | L-Glu | | 106 ± 7 |

TABLE 2-continued

Structures and uncoupling bioactivity for exemplary chemical uncouplers with various head groups.

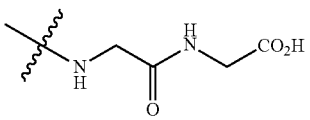 [SMILES: *NCC(=O)NCC(=O)O]

| Compound | Head group name | R = | % stimulation of respiration (baseline = 100%) |
|---|---|---|---|
| 12 | Gly-Gly | 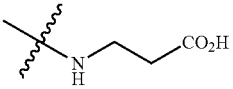 [SMILES: *NCCC(=O)O] | 206 ± 32 |
| 13 | Homoglycine | 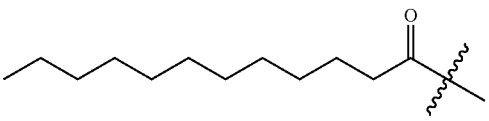 [SMILES: *C(=O)CCCCCCCCCCC] | 185 ± 10 |

Uncoupling bioactivity for exemplary chemical uncouplers of the disclosure with various fatty acid side chains is provided below in Table 3.

TABLE 3

Structures and uncoupling bioactivity for exemplary chemical uncouplers with various fatty acid side chains.

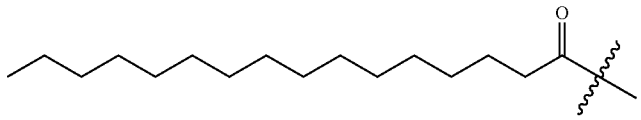 [SMILES: *C(=O)CCCCCCCCCCCCCCC]

| Cmpd | Fatty acid name | R' = | % stimulation of respiration (baseline = 100%) |
|---|---|---|---|
| 14 | C12:0 | 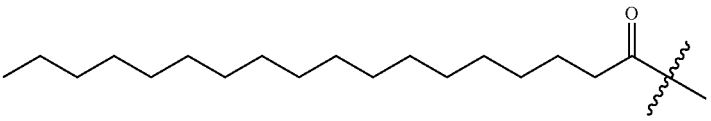 [SMILES: *C(=O)CCCCCCCCCCCCCCCCC] | 96 ± 4 |
| 15 | C16:0 | | 180 ± 20 |
| 16 | C18:0 | | 148 ± 12 |
| 17 | C20:0 | 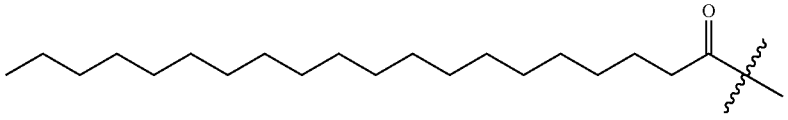 [SMILES: *C(=O)CCCCCCCCCCCCCCCCCCC] | 95 ± 8 |

TABLE 3-continued

Structures and uncoupling bioactivity for exemplary chemical uncouplers with various fatty acid side chains.

| Cmpd | Fatty acid name | R' = | % stimulation of respiration (baseline = 100%) |
|---|---|---|---|
| 18 | C22:0 | | 100 ± 3 |
| 19 | C18:2 | | 218 ± 10 |
| 20 | C18:3 | | 109 ± 12 |
| 21 | trans-C18:1 | | 107 ± 3 |
| 22 | $\Delta^6$-C18:1 | | 110 ± 12 |
| 23 | $\Delta^{11}$-C18:1 | | 115 ± 8 |
| 24 | C20:1 | | 103 ± 3 |
| 25 | C20:4 | | 200 ± 12 |

TABLE 3-continued

Structures and uncoupling bioactivity for exemplary chemical uncouplers with various fatty acid side chains.

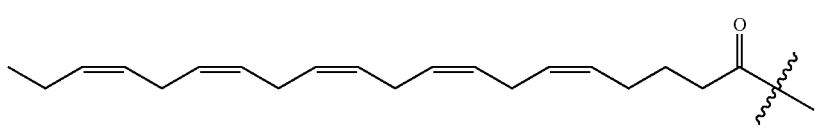 [SMILES: *C(=O)CCC/C=C\C/C=C\C/C=C\C/C=C\C/C=C\CC]

| Cmpd | Fatty acid name | R' = | % stimulation of respiration (baseline = 100%) |
|---|---|---|---|
| 26 | C20:5 | 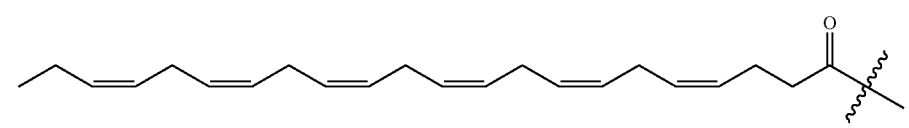 [SMILES: *C(=O)CC/C=C\C/C=C\C/C=C\C/C=C\C/C=C\C/C=C\CC] | 259 ± 43 |
| 27 | C22:6 | 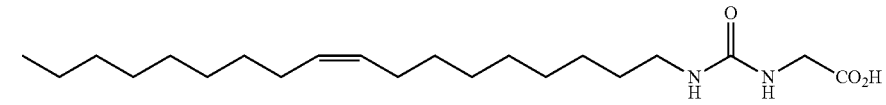 | 166 ± 11 |

Uncoupling bioactivity for exemplary urea chemical uncouplers is provided below in Table 4.

TABLE 4

Structures and uncoupling bioactivity for exemplary chemical uncouplers with various head groups.

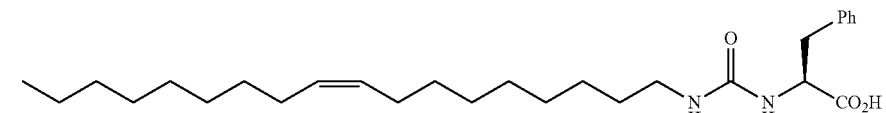

| Compound | Structure | % stimulation of respiration (baseline = 100%) |
|---|---|---|
| 28 | 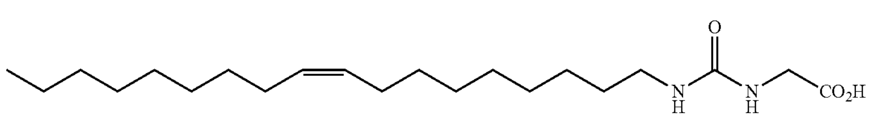 [SMILES: CCCCCCCC/C=C\CCCCCCCCNC(=O)NCC(=O)O] | 104 ± 3 |
| 29 | 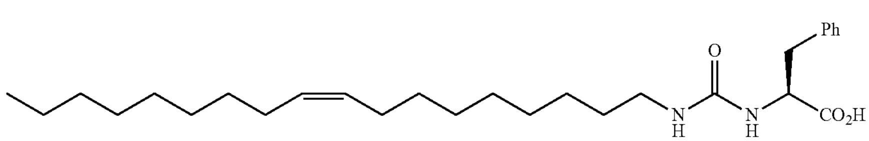 [SMILES: CCCCCCCC/C=C\CCCCCCCCNC(=O)N[C@@H](Cc1ccccc1)C(=O)O] | 97 ± 5 |

Uncoupling bioactivity for exemplary chemical uncouplers of the disclosure with various head groups is provided below in Table 5.

TABLE 5

Structures and uncoupling bioactivity for exemplary chemical uncouplers with various head groups.

C18:1

C18:2

| Compound | Fatty acid | R = | % stimulation of respiration (baseline = 100%) |
|---|---|---|---|
| 30 | C18:1 | 2-piperidinecarboxylic acid | 174 ± 3 |
| 31 | C18:1 | 1,2,3,4-tetrahydroisoquinoline-3-carboxylic acid | 187 ± 19 |
| 32 | C18:1 | 1,2,3,4-tetrahydroisoquinoline-1-carboxylic acid | 216 ± 17 |
| 33 | C18:1 | isoindoline-1-carboxylic acid | 240 ± 24 |
| 34 | C18:1 | isoindoline-1-carboxylic acid (epimer) | 190 ± 12 |
| 35 | C18:1 | indoline-2-carboxylic acid | 146 ± 5 |
| 36 | C18:2 | isoindoline-1-carboxylic acid | 185 ± 18 |

TABLE 5-continued

Structures and uncoupling bioactivity for exemplary chemical uncouplers with various head groups.

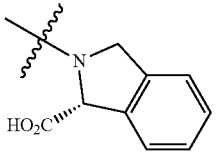 [SMILES: *N1Cc2ccccc2[C@@H]1C(=O)O]

| Compound | Fatty acid | R = | % stimulation of respiration (baseline = 100%) |
|---|---|---|---|
| 37 | C18:2 | | 190 ± 12 |

Example 4: N-Acyl Amino Acids and Derivatives as Inhibitors of PM20DJ

Some of the chemical uncouplers of the disclosure are entirely resistant to hydrolysis by PM20D1 (e.g., compounds 33, 34, 36, and 37; FIG. 3). Without wishing to be bound by any theory, the compounds of the disclosure, or their derivatives, may act as competitive inhibitors of the PM20D1 active site. Accordingly, treatment of mice with these compounds may block PM20D1 activity, dysregulate endogenous N-acyl amino acids, and also cause anti-nociceptive behaviors. The disclosed compounds thus may useful for the treatment of a variety of pain conditions, including but not limited to neuropathic pain, osteoarthritis, dental pain, rheumatoid arthritis, cancer-associated pain, bone pain, nerve pain, lower back pain, and fibromyalgia.

Example 5: In Vivo Activity of N-Acyl Amino Acids and Derivatives

Treatment of Mice with Compounds

Figure 4A:
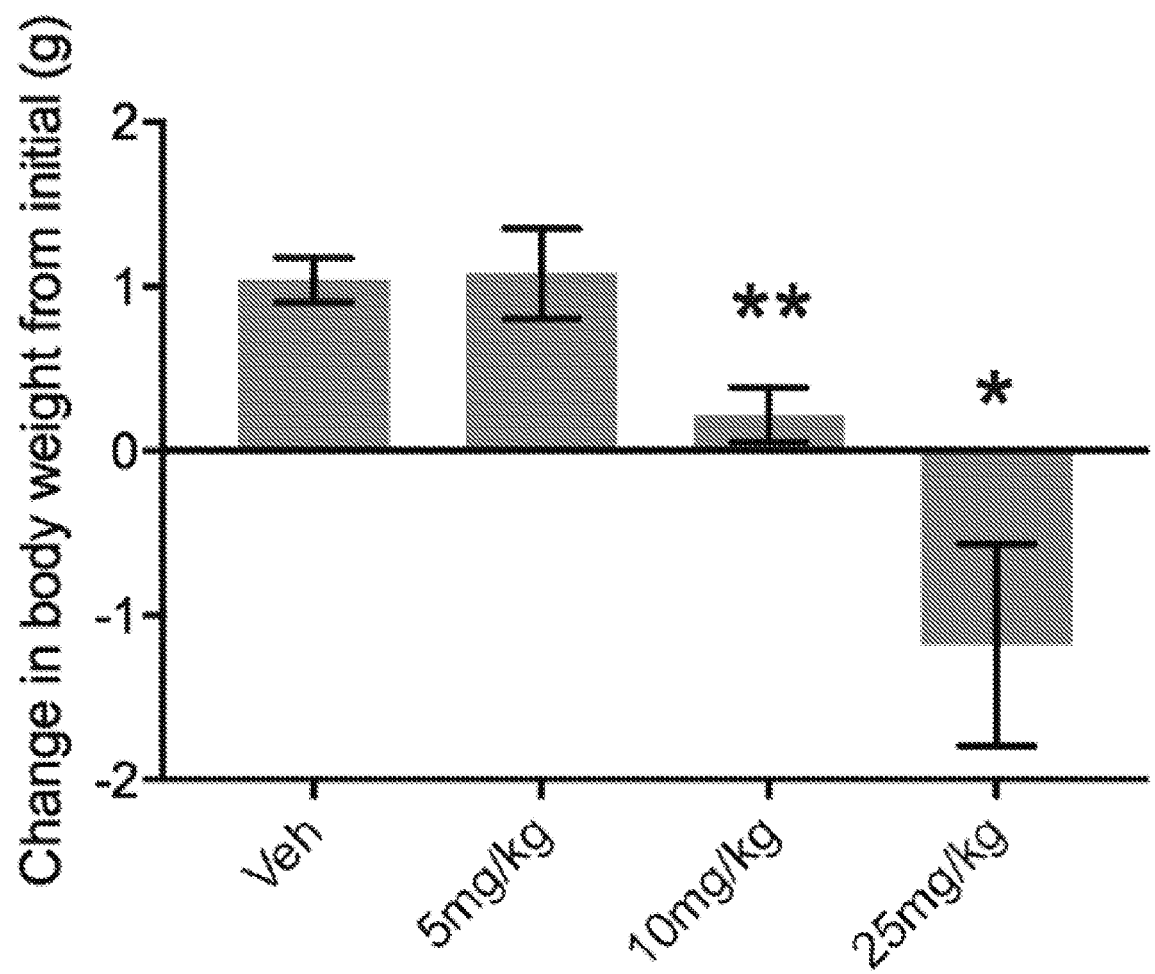
FIG. 4A shows the change in body weight from the initial weight in mice after treatment with different doses of an exemplary compound of the disclosure.
Figure 4B:
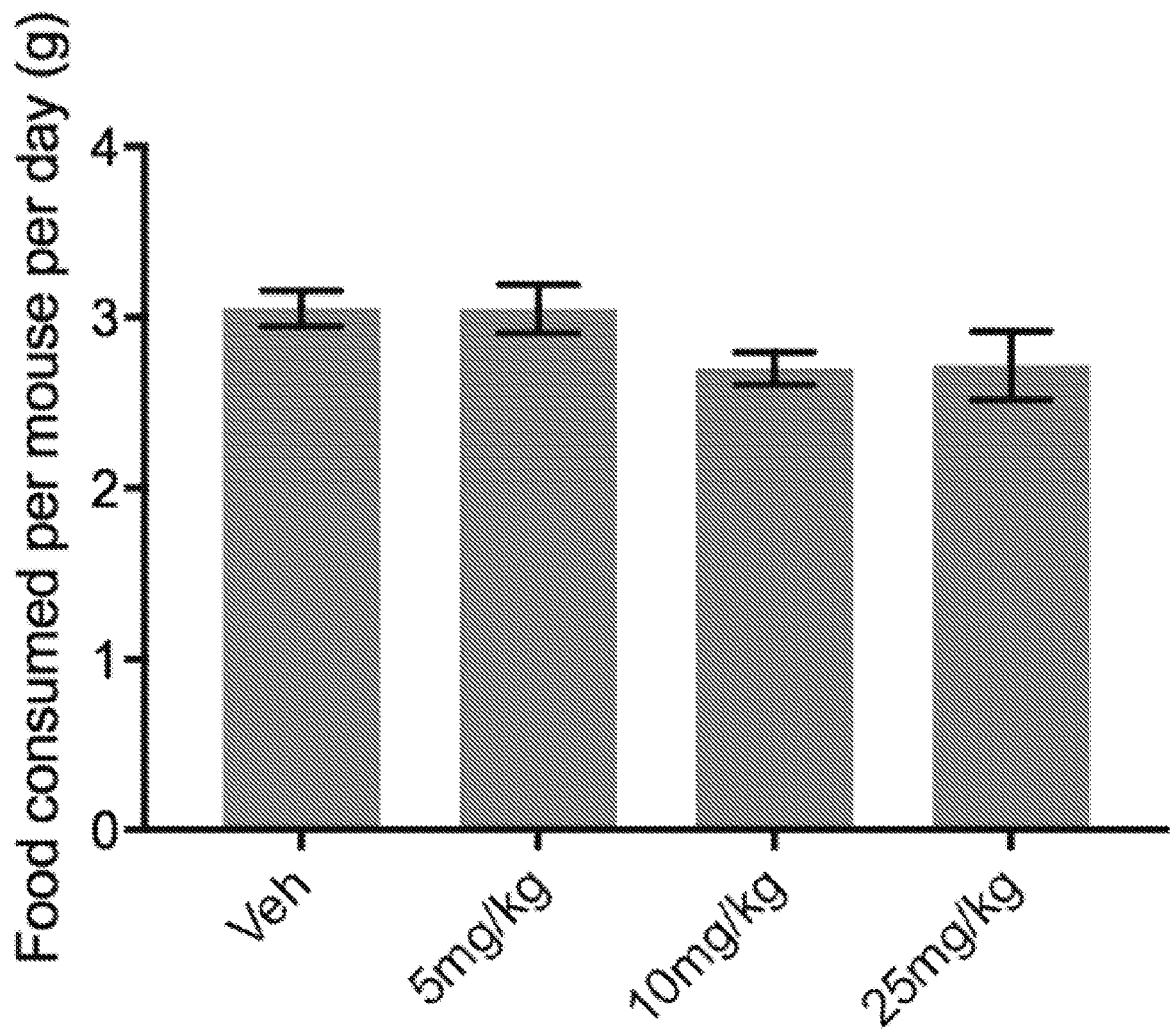
FIG. 4 shows the average food consumed per mouse per day in mice treated with different doses of an exemplary compound of the disclosure.

An exemplary chemical uncoupler of the disclosure, compound 33, possesses uncoupling bioactivity in vivo. On average, mice in the different treatment groups consumed the same amount of food per mouse per day. Mice treated with higher doses of compound 33 showed a statistically significant weight loss over time (FIGS. 4A and 4B).

DIO mice (19 weeks, males, stock #380050) were purchased from The Jackson Laboratory. Mice were maintained on a high fat diet for the duration of the experiment (60% fat, Research Diets). Prior to compound administration, mice were mock injected with vehicle (18:1:1 v/v/v saline:DMSO:Kolliphor EL, intraperitoneal) for 4 days. Compound 33 was prepared in the same vehicle and administered at 5 µl/g body weight at the indicated doses. Administration of vehicle of compound occurred once per day. Data shown in FIG. 4A compared changes in body weights of representative mice at day 7 versus initial weight on day 0. Data shown in FIG. 4B represented average food intake per mouse over the 7 day dosing period for each treatment group.

PM20D1-Knockout Mice

PM20D1-KO mice have been generated. These mice had abolished tissue and blood N-acyl amino acid hydrolase activity and dysregulated circulating and tissue N-acyl amino acids. These data demonstrated that PM20D1 was the major mammalian enzyme responsible for regulating endogenous N-acyl amino acid levels. Remarkably, PM20D1-KO mice showed anti-nociceptive phenotypes in a variety of chronic and/or inflammatory pain models such as the acetic acid constriction assay and the formalin assay. Without wishing to be bound by any theory, the data suggested that inhibitors of PM20D1 may be useful for the treatment of pain.

Pharmacokinetic Properties

Figure 5:
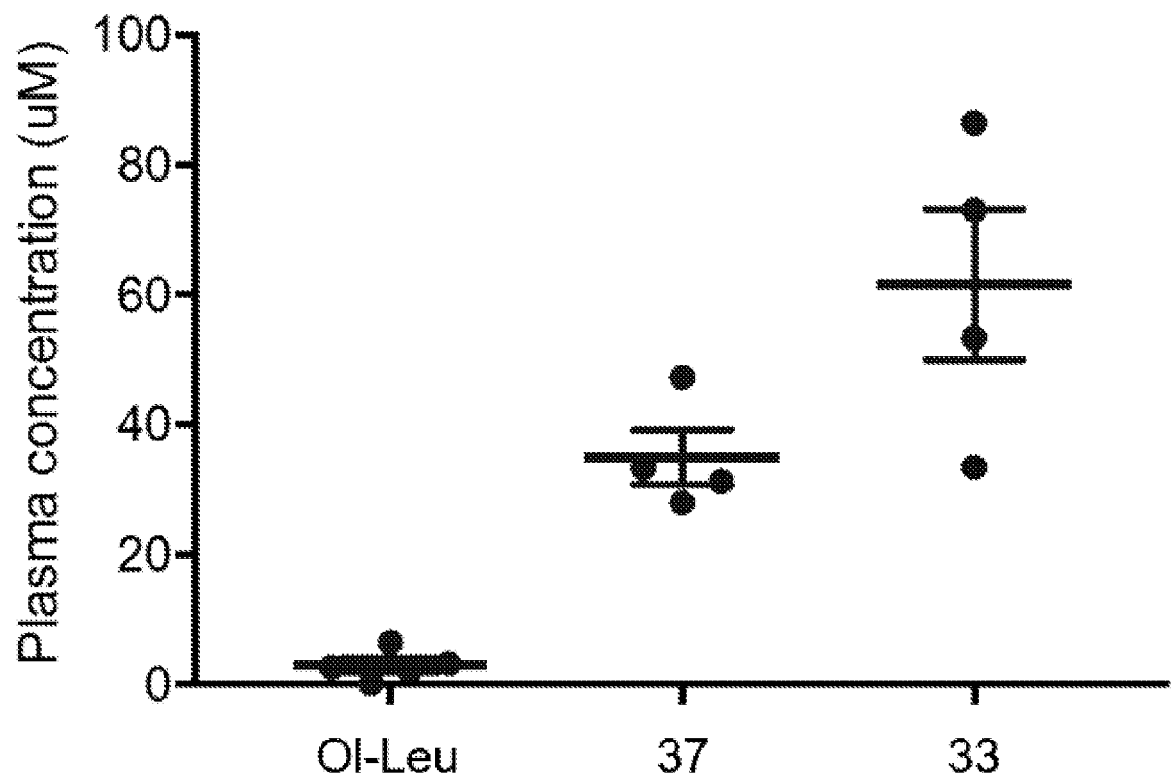
FIG. 5 shows the plasma concentration 1 hour after a 10 mg/kg dose of exemplary compounds of the disclosure.

Exemplary chemical uncouplers of the disclosure, compounds 33 and 37, showed augmented pharmacokinetic properties in vivo (FIG. 5).

DIO mice (19 weeks, males, stock #380050) were purchased from The Jackson Laboratory. Prior to compound administration, mice were mock injected with vehicle (18:1:1 v/v/v saline:DMSO:Kolliphor EL) for 4 days. Compounds 33 and 37 were prepared in the same vehicle and administered at 10 mg/kg doses. Plasma concentration was measured 1 hour after compound administration.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the present disclosure described herein. Such equivalents are intended to be encompassed by the following claims.

What is claimed is:

1. A compound represented by Formula (Id), or a pharmaceutically acceptable salt thereof:

Formula (Id)

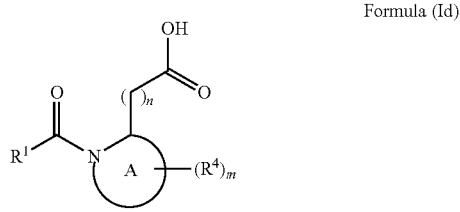

wherein ring A is

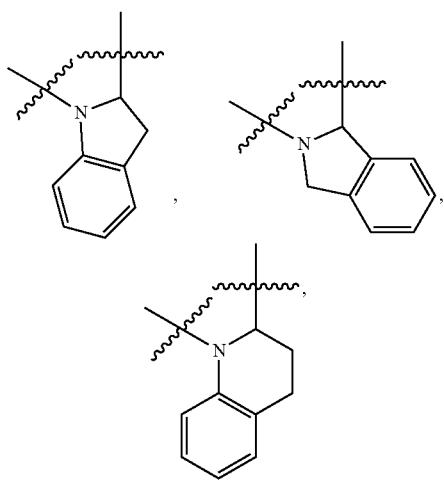

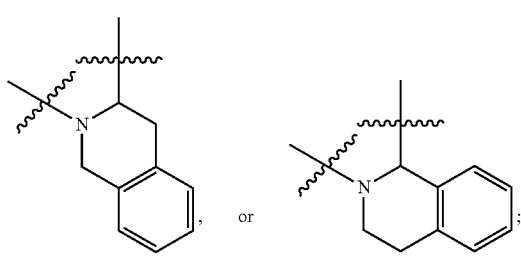 [SMILES: *C1Cc2ccccc2CN1* ; *C1c2ccccc2CCN1*]

or $R^1$ is $(C_{10}-C_{30})$alkyl, $(C_{10}-C_{30})$alkene, or $(C_{10}-C_{30})$alkyne; wherein $(C_{10}-C_{30})$alkyl, $(C_{10}-C_{30})$alkene, or $(C_{10}-C_{30})$alkyne is optionally substituted with one, two, three, or four substituents independently selected from the group consisting of $(C_1-C_6)$alkyl, $(C_1-C_6)$alkyloxy, cycloalkyl, and heterocycloalkyl;

$R^3$ is H or $(C_1-C_6)$alkyl;

$R^4$ is halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and —N(R$^3$)—C(=NH)—N(R$^3$)$_2$;

m is an integer from 0-4; and n is an integer from 0-5.

2. The compound of claim 1, wherein $R^1$ is $(C_{12}-C_{22})$alkyl or $(C_{12}-C_{22})$alkene;

$R^3$ is H or $(C_1-C_6)$alkyl;

$R^4$ is halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and —N(R$^3$)—C(=NH)—N(R$^3$)$_2$;

m is an integer from 0-4; and n is an integer from 0-3.

3. The compound of claim 1, wherein $R^1$ is $(C_{12}-C_{22})$alkyl or $(C_{12}-C_{22})$alkene; wherein $(C_{12}-C_{22})$alkyl or $(C_{12}-C_{22})$alkene is optionally substituted with one or two substituents independently selected from the group consisting of $(C_1-C_6)$alkyl and cycloalkyl;

$R^3$ is H or $(C_1-C_6)$alkyl;

$R^4$ is halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and —N(R$^3$)—C(=NH)—N(R$^3$)$_2$; and m is an integer from 0-2; and n is an integer from 0-3.

4. The compound of claim 1, wherein m is an integer from 0-2.

5. The compound of claim 1, wherein each $R^4$ is independently selected from the group consisting of halogen, CN, —NO$_2$, —OR$^3$, —SR$^3$, and $(C_1-C_6)$alkyl.

6. The compound of claim 1, wherein n is 0.

7. The compound of claim 1, wherein $R^1$ is $(C_{10}-C_{22})$alkyl or $(C_{10}-C_{22})$alkene.

8. The compound of claim 7, wherein $R^1$ is $(C_{12}-C_{22})$alkyl or $(C_{12}-C_{22})$alkene.

9. The compound of claim 1, wherein $R^1$ is selected from the group consisting of $C_{12}$, $C_{14}$, $C_{16}$, C16:1, $C_{18}$, C18:1, C18:2, C18:3, $C_{20}$, C20:1, C20:4, C20:5, $C_{22}$, C22:1, and C22:6.

10. The compound of claim 1 selected from the group consisting of

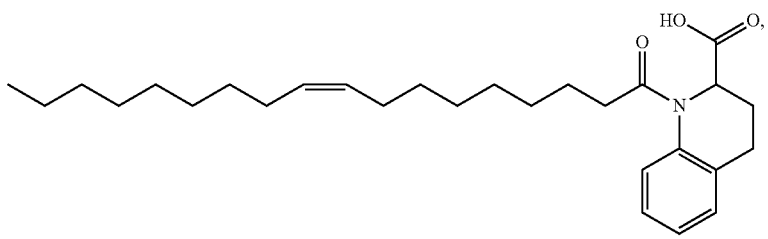

-continued
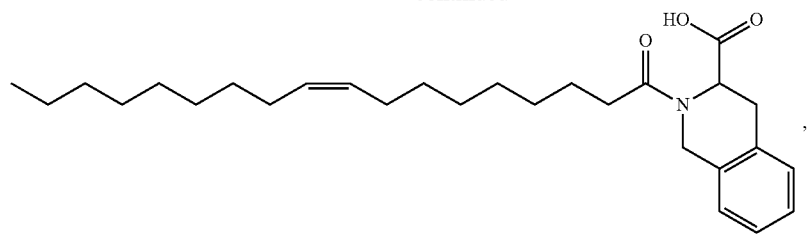
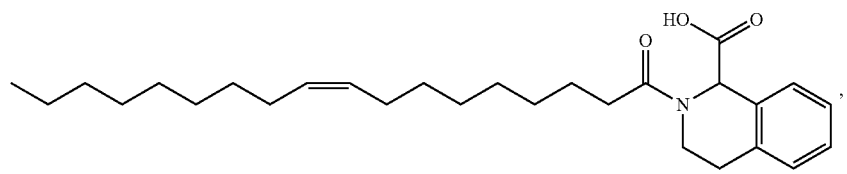
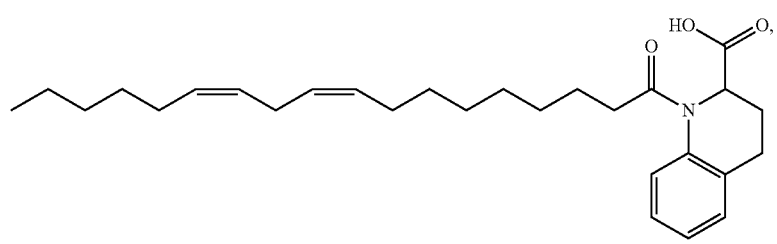
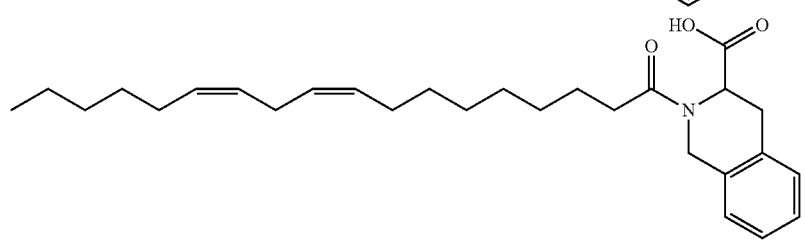
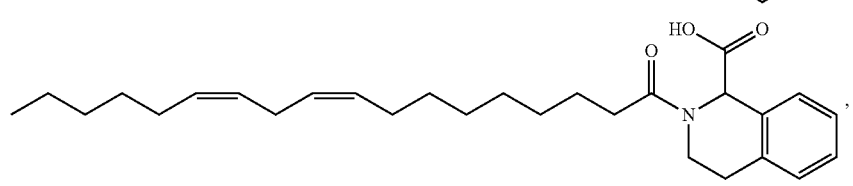
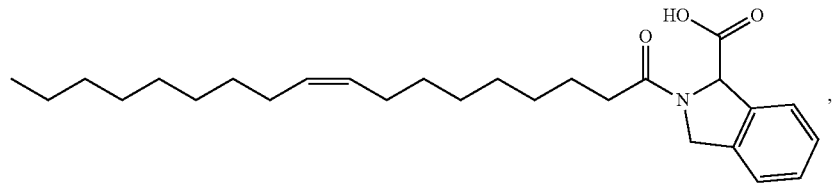
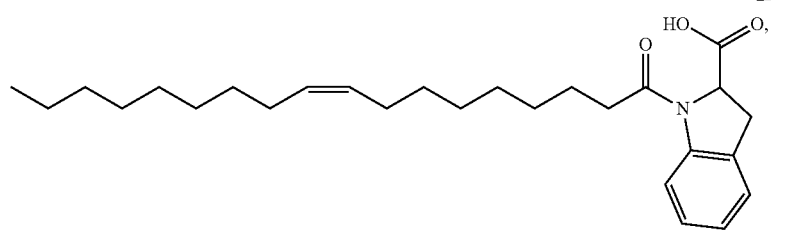
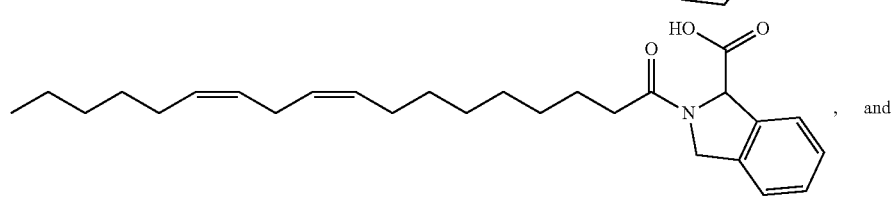

11. A method of for modulating a metabolic response comprising contacting a cell with a compound represented by Formula (Id) or a pharmaceutically acceptable salt thereof:

Formula (Id)

wherein
ring A is a polycyclic ring system having two or more carbon atoms common between two adjoining rings, wherein at least one ring is aromatic and the other ring is heterocyclyl;
$R^1$ is $(C_{10}$-$C_{30})$alkyl, $(C_{10}$-$C_{30})$alkene, or $(C_{10}$-$C_{30})$alkyne; wherein $(C_{10}$-$C_{30})$alkyl, $(C_{10}$-$C_{30})$alkene, or $(C_{10}$-$C_{30})$alkyne is optionally substituted with one, two, three, or four substituents independently selected from the group consisting of $(C_1$-$C_6)$alkyl, $(C_1$-$C_6)$alkyloxy, cycloalkyl, and heterocycloalkyl;
$R^3$ is H or $(C_1$-$C_6)$alkyl;
$R^4$ is halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and N(R$^3$)—C(=NH)—N(R$^3$)$_2$;
m is an integer from 0-4; and
n is an integer from 0-5,
thereby modulating the metabolic response.

12. A method of treating pain in a subject comprising administering to the subject a therapeutically effective amount of compound represented by Formula (Id) or a pharmaceutically acceptable salt thereof:

Formula (Id)

wherein
ring A is (i) a polycyclic ring system having two or more carbon atoms common between two adjoining rings, wherein at least one ring is aromatic and the other ring is heterocyclyl or (ii) a heteroaryl;
$R^1$ is $(C_{10}$-$C_{30})$alkyl, $(C_{10}$-$C_{30})$alkene, or $(C_{10}$-$C_{30})$alkyne; wherein $(C_{10}$-$C_{30})$alkyl, $(C_{10}$-$C_{30})$alkene, or $(C_{10}$-$C_{30})$alkyne is optionally substituted with one, two, three, or four substituents independently selected from the group consisting of $(C_1$-$C_6)$alkyl, $(C_1$-$C_6)$alkyloxy, cycloalkyl, and heterocycloalkyl;
$R^3$ is H or $(C_1$-$C_6)$alkyl;
$R^4$ is halogen, —CN, —NO$_2$, —OR$^3$, —SR$^3$, —N(R$^3$)$_2$, —(C$_1$-C$_6$)alkyl, —C(O)OR$^3$, —C(O)N(R$^3$)$_2$, —N(R$^3$)C(O)R$^3$, —N(R$^3$)C(O)OR$^3$, and N(R$^3$)—C(=NH)—N(R$^3$)$_2$;
m is an integer from 0-4; and
n is an integer from 0-5,
thereby treating pain in the subject.

13. The method of claim 12, wherein the pain is selected from the group consisting of neuropathic pain, osteoarthritis, dental pain, rheumatoid arthritis, cancer-associated pain, bone pain, nerve pain, lower back pain, and fibromyalgia.

14. The method of claim 12, wherein the subject is a non-human animal or a human.

15. The method of claim 11, wherein ring A is selected from the group consisting of

16. The method of claim 11, wherein the compound is selected from the group consisting of
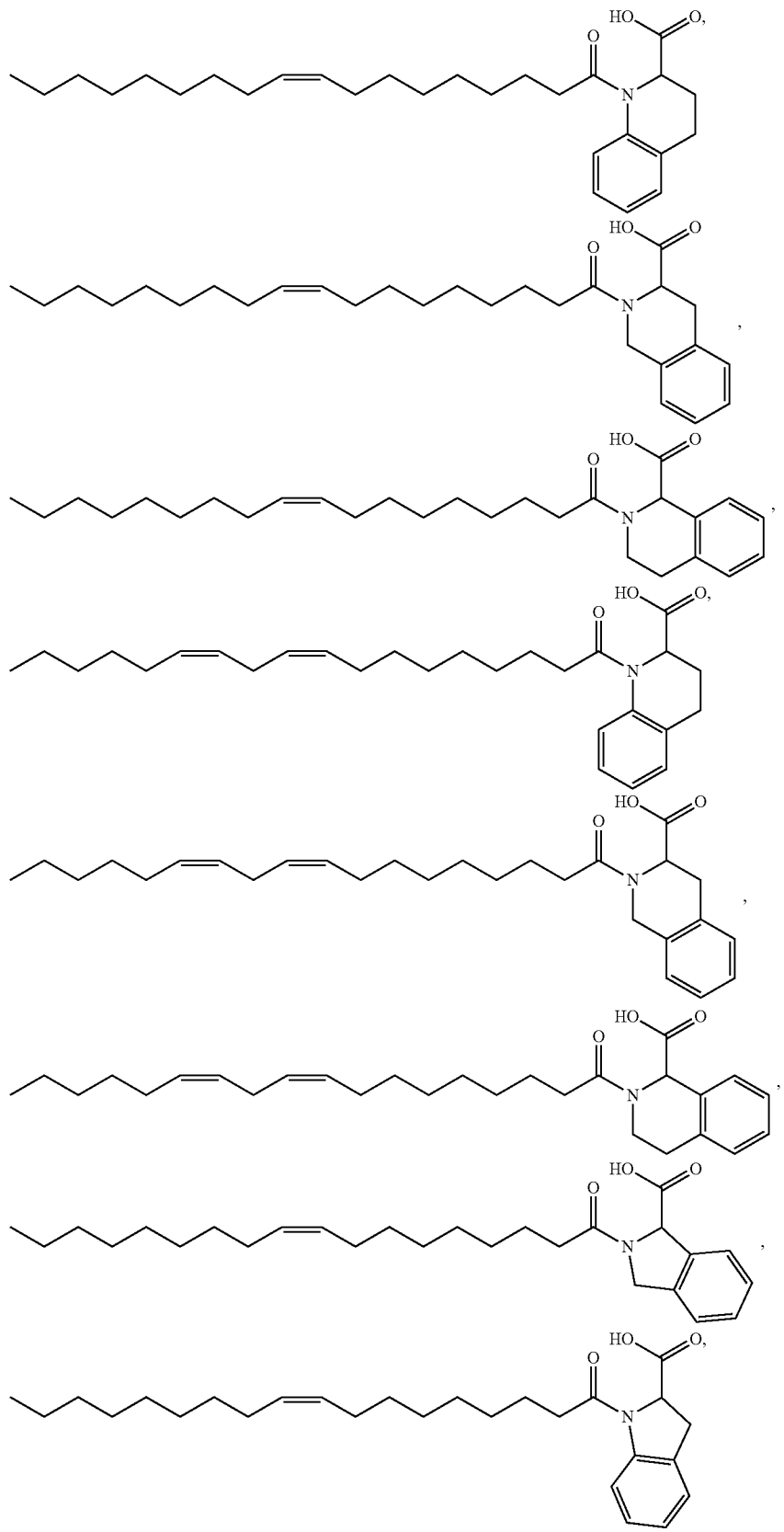

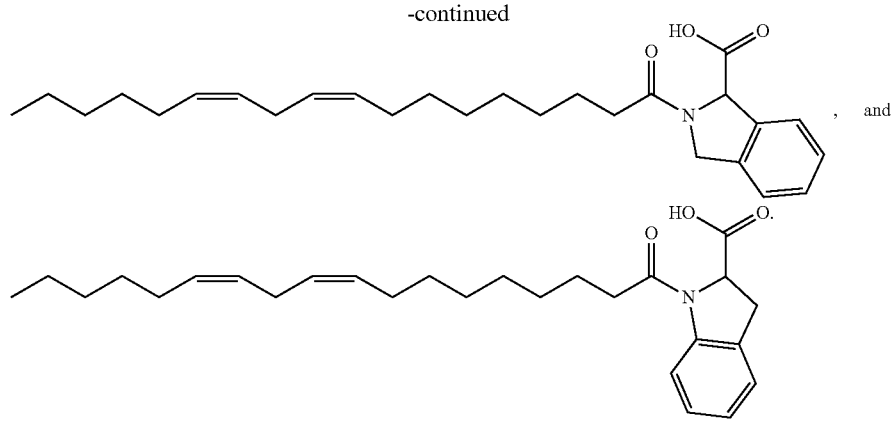
17. The method of claim 12, wherein ring A is selected from the group consisting of
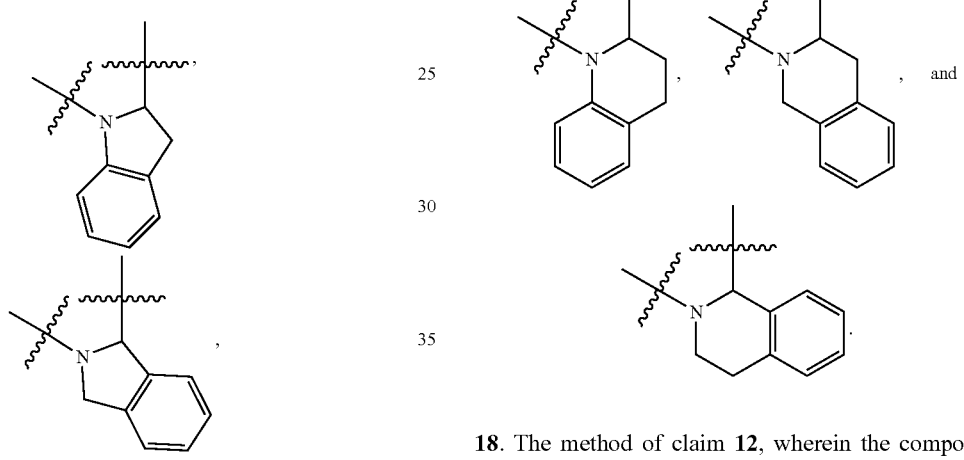
18. The method of claim 12, wherein the compound is selected from the group consisting of
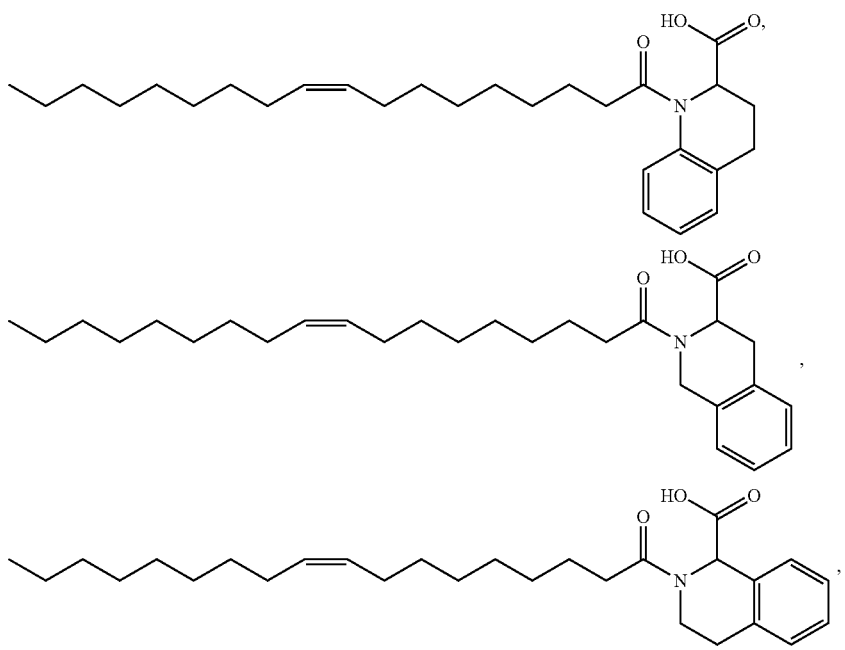

-continued
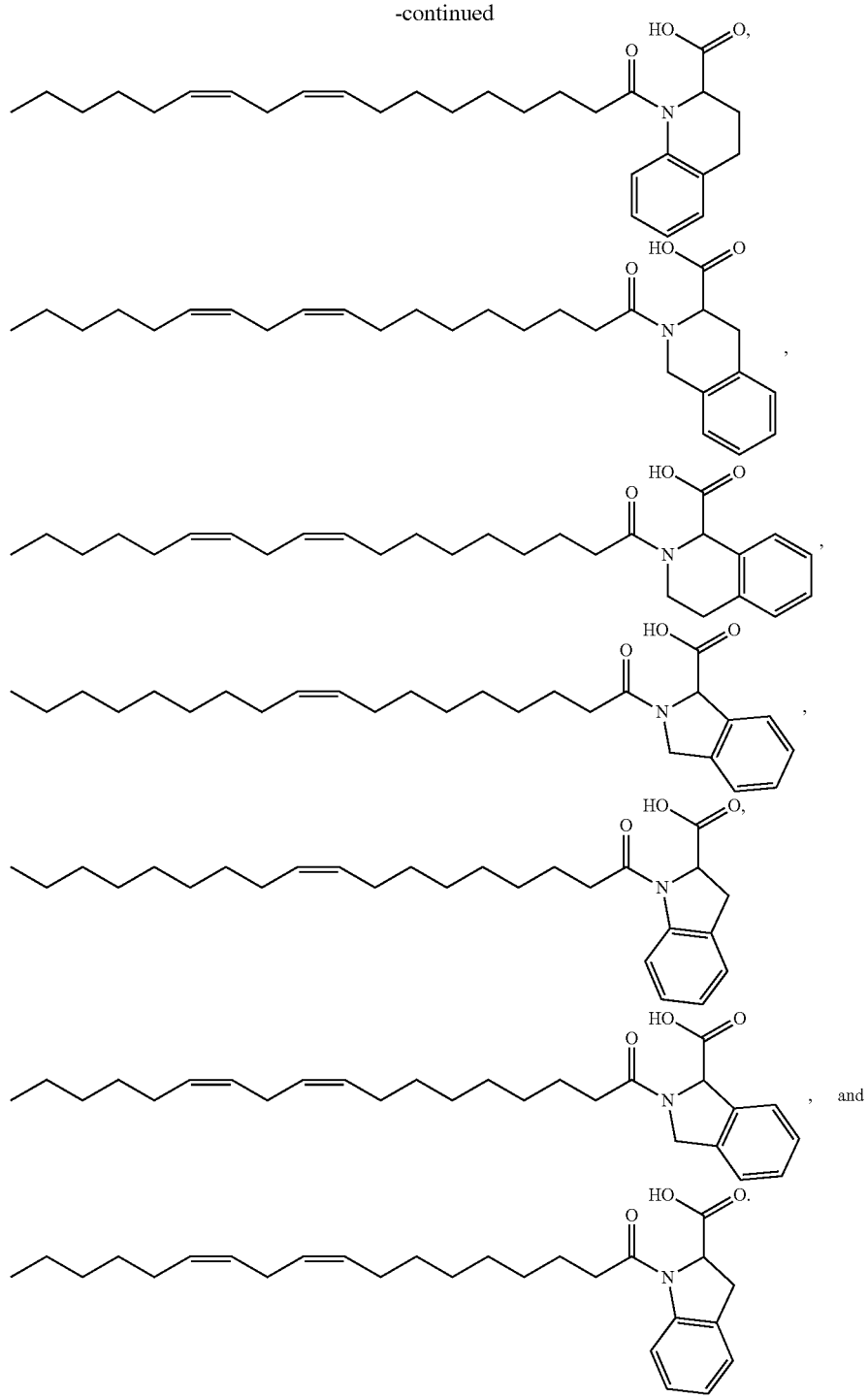
19. The method of claim 12, wherein ring A is a polycyclic ring system having two or more carbon atoms common between two adjoining rings, wherein at least one ring is aromatic and the other ring is heterocyclyl.
* * * * *